(12) United States Patent
Hirschel et al.

(10) Patent No.: US 10,569,019 B2
(45) Date of Patent: Feb. 25, 2020

(54) SUBSTANCE DISPENSING DEVICE WITH SIGNALING DEVICE

(71) Applicant: TecPharma Licensing AG, Burgdorf (CH)

(72) Inventors: Jürg Hirschel, Bern (CH); Markus Tschirren, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 205 days.

(21) Appl. No.: 14/858,755

(22) Filed: Sep. 18, 2015

(65) Prior Publication Data

US 2016/0008541 A1  Jan. 14, 2016

Related U.S. Application Data

(63) Continuation of application No. PCT/CH2014/000034, filed on Mar. 20, 2014.

(30) Foreign Application Priority Data

Mar. 22, 2013  (EP) .................................... 13160614

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3157* (2013.01); *A61M 5/3129* (2013.01);
(Continued)

(58) Field of Classification Search
CPC .......... A61M 5/3157; A61M 2205/581; A61M 5/2033; A61M 5/20; A61M 5/3129;
(Continued)

(56) References Cited

U.S. PATENT DOCUMENTS

| 1,819,258 A | 8/1931 | Mendel |
| 2008/0262438 A1 | 10/2008 | Bollenbach et al. |

(Continued)

FOREIGN PATENT DOCUMENTS

| DE | 10359694 A1 | 7/2005 |
| DE | 102007013836 | 9/2008 |

(Continued)

OTHER PUBLICATIONS

International Search Report dated Jun. 12, 2014, for International Application No. PCT/CH2014/000034, 3 pages.

(Continued)

*Primary Examiner* — Nilay J Shah
(74) *Attorney, Agent, or Firm* — Dorsey & Whitney LLP

(57) ABSTRACT

Device for dispensing a substance having: a dispensing element through which the substance can be dispensed, a displaceable protective element for the dispensing element, a drive element that is coupled with the protective element and a feedback element which can generate a signal when or after a predefined quantity or the entire quantity of the substance to be dispensed has been dispensed characterized in that the feedback device is coupled with the drive element.

19 Claims, 23 Drawing Sheets

(51) Int. Cl.
*A61M 5/31* (2006.01)
*A61M 5/32* (2006.01)

(52) U.S. Cl.
CPC .......... *A61M 5/3204* (2013.01); *A61M 5/326* (2013.01); *A61M 5/3243* (2013.01); *A61M 5/3257* (2013.01); *A61M 2005/2013* (2013.01); *A61M 2005/3109* (2013.01); *A61M 2005/3143* (2013.01); *A61M 2205/581* (2013.01); *A61M 2205/582* (2013.01)

(58) Field of Classification Search
CPC ...... A61M 2005/3143; A61M 5/31565; A61M 2005/206; A61M 2005/3258; A61M 2005/3254; A61M 2005/3252; A61M 5/3257; A61M 5/326; A61M 5/3287; A61M 5/3234; A61M 5/3243; A61M 5/3245
See application file for complete search history.

(56) References Cited

U.S. PATENT DOCUMENTS

| | | | |
|---|---|---|---|
| 2010/0036320 A1* | 2/2010 | Cox | A61M 5/24 604/135 |
| 2010/0137798 A1 | 6/2010 | Streit et al. | |
| 2011/0196339 A1 | 8/2011 | Hirschel et al. | |
| 2011/0218500 A1* | 9/2011 | Grunhut | A61M 5/2033 604/228 |
| 2016/0008542 A1 | 1/2016 | Hirschel et al. | |

FOREIGN PATENT DOCUMENTS

| | | | |
|---|---|---|---|
| DE | 102008037310 A1 | 7/2010 | |
| EP | 2489380 A1 * | 8/2012 | .......... A61M 5/3158 |
| JP | 2008229344 A | 10/2008 | |
| WO | WO 1994/011041 | 5/1994 | |
| WO | 2004047892 A1 | 6/2004 | |
| WO | 2010017650 A1 | 2/2010 | |
| WO | WO 2011/043714 | 4/2011 | |
| WO | 2011101381 A2 | 8/2011 | |
| WO | WO 2011/123024 | 10/2011 | |
| WO | 2012110577 A1 | 8/2012 | |
| WO | 2012117255 A1 | 9/2012 | |
| WO | WO 2013/016832 | 2/2013 | |

OTHER PUBLICATIONS

"International Search Report dated Jun. 25, 2014, for International Application No. PCT/CH2014/000035", 2 pages.

* cited by examiner

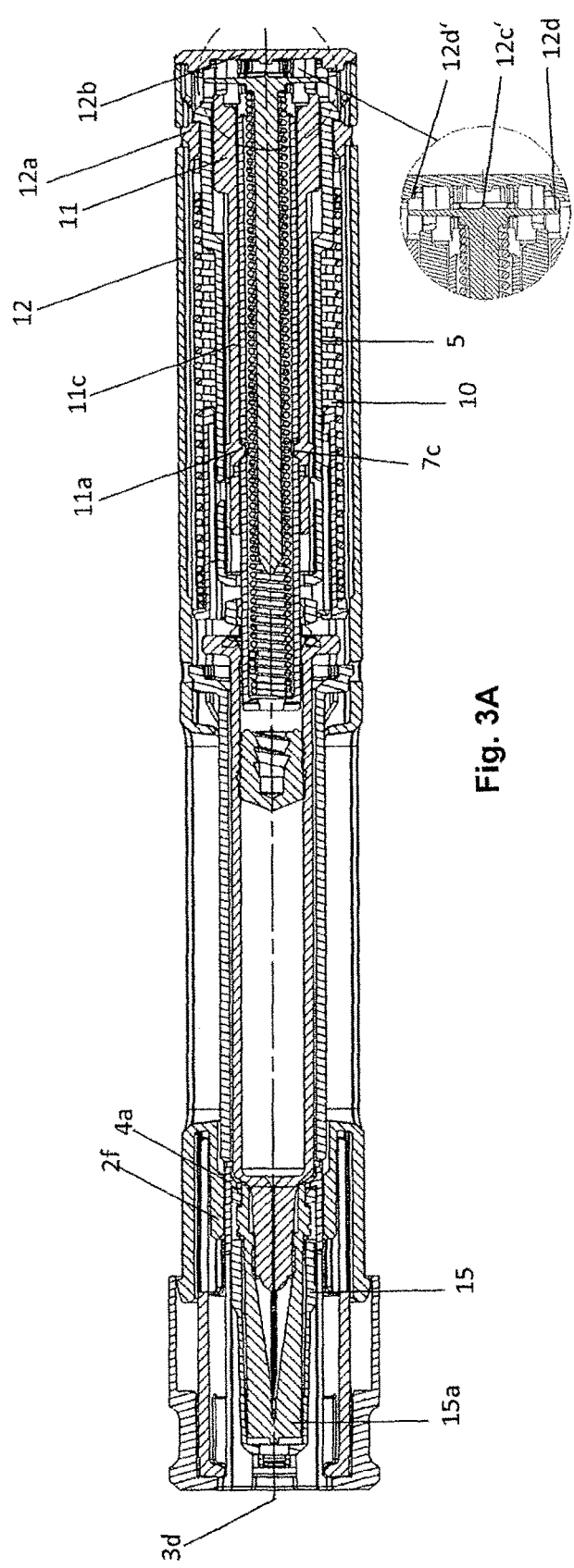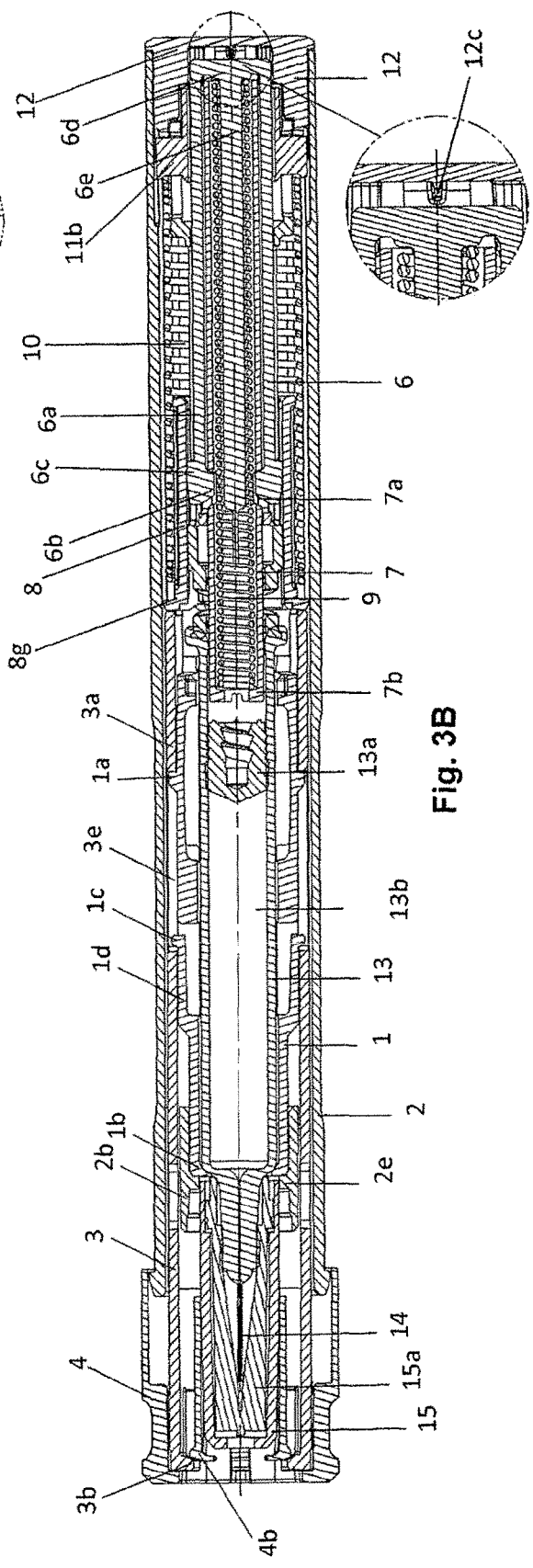
Fig. 3A
Fig. 3B

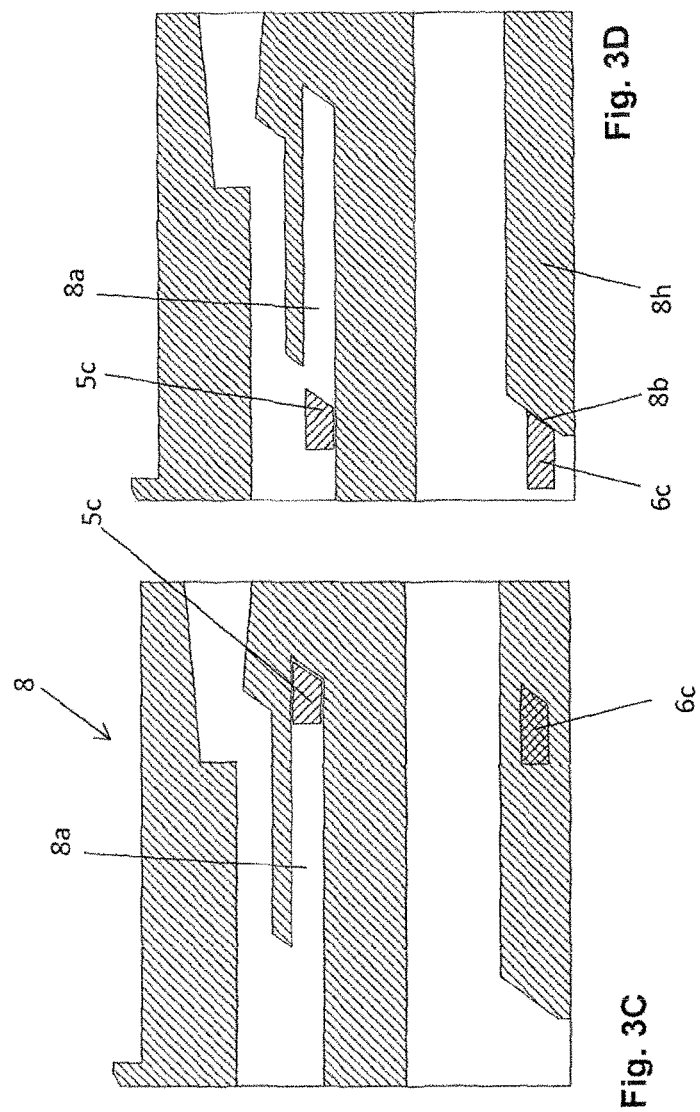
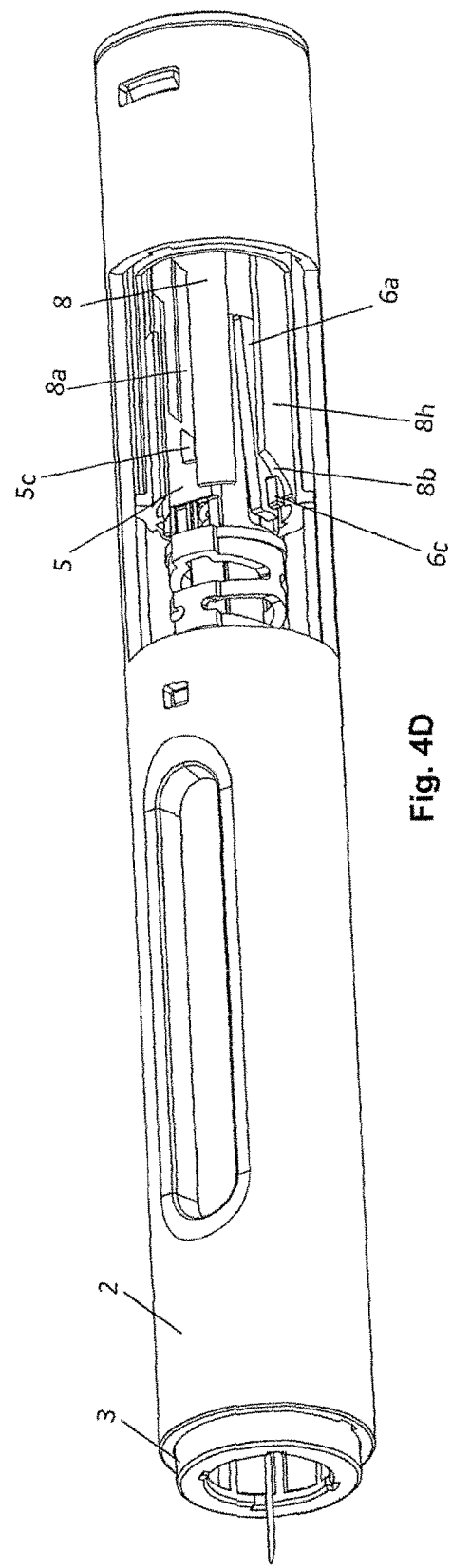
Fig. 3C
Fig. 3D
Fig. 4D

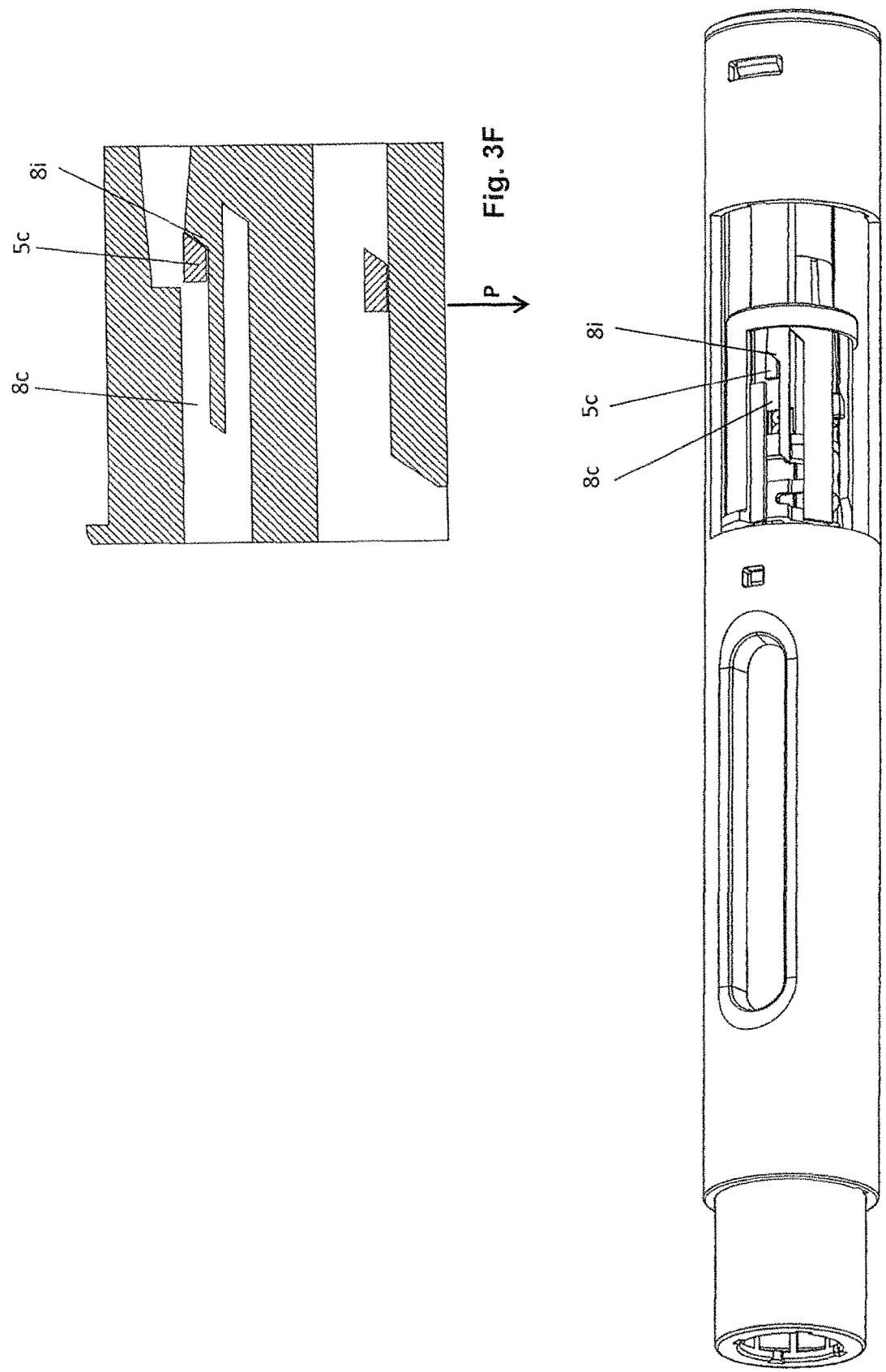

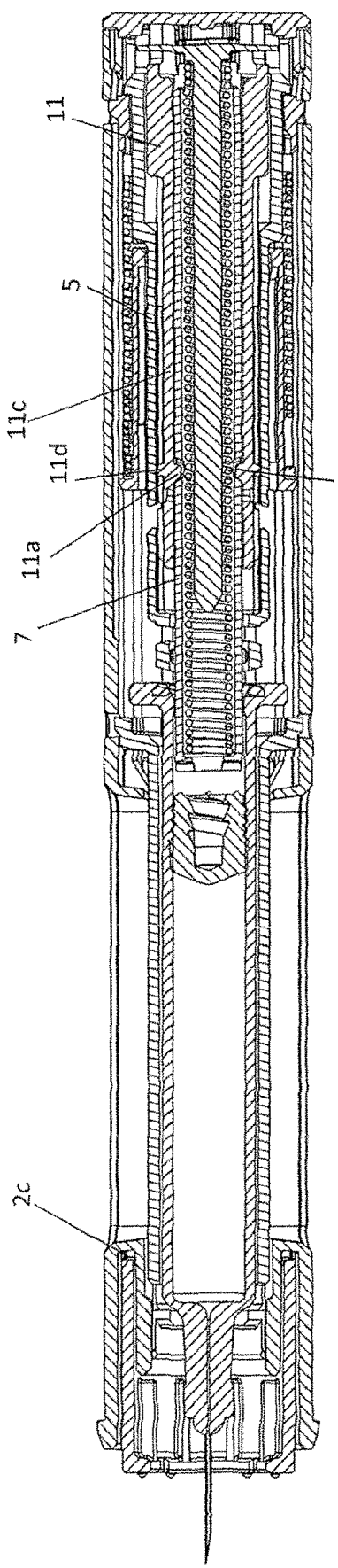
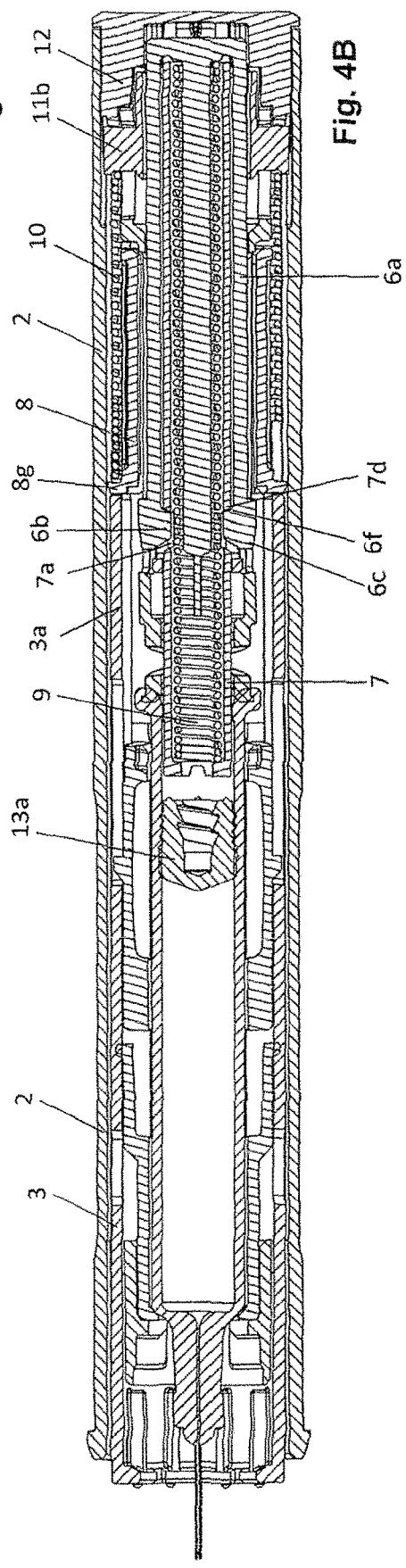

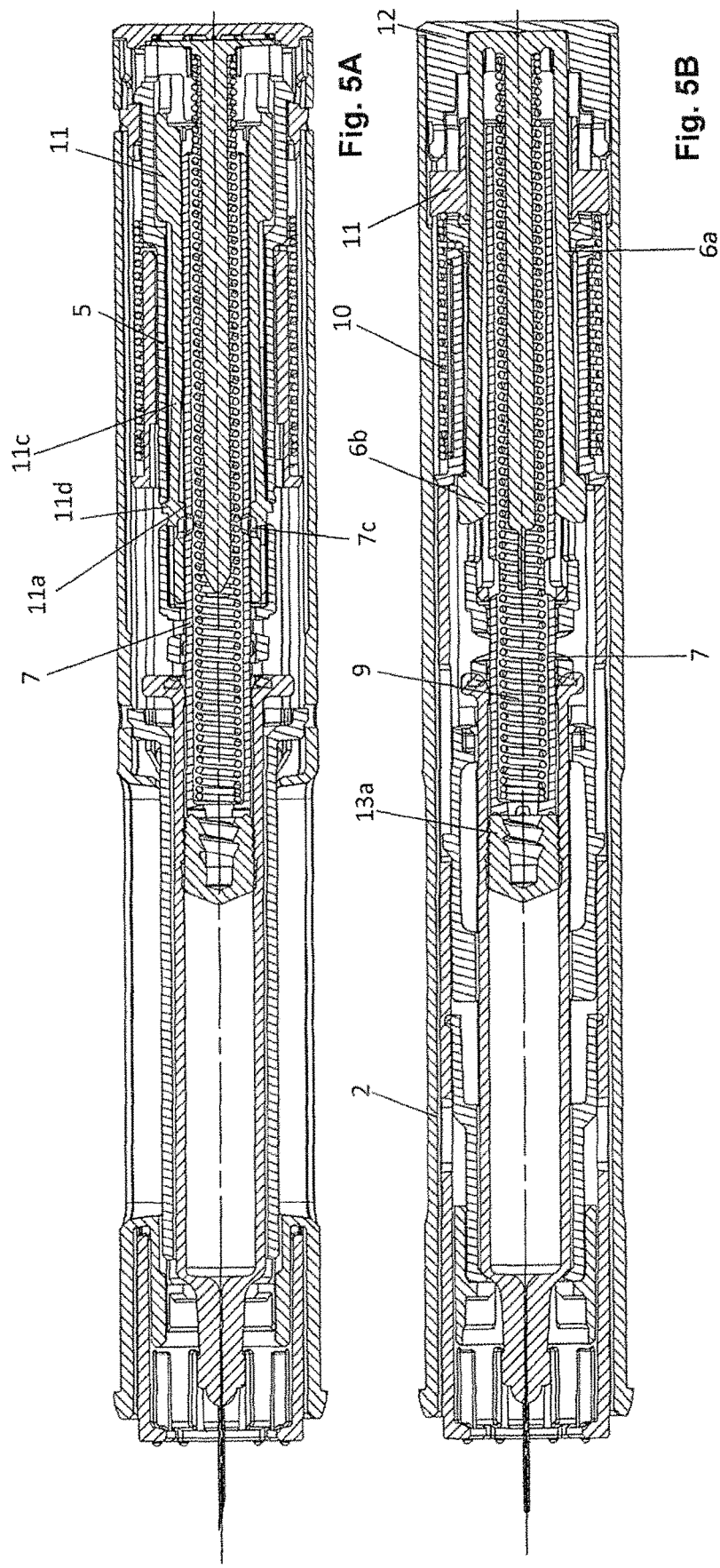

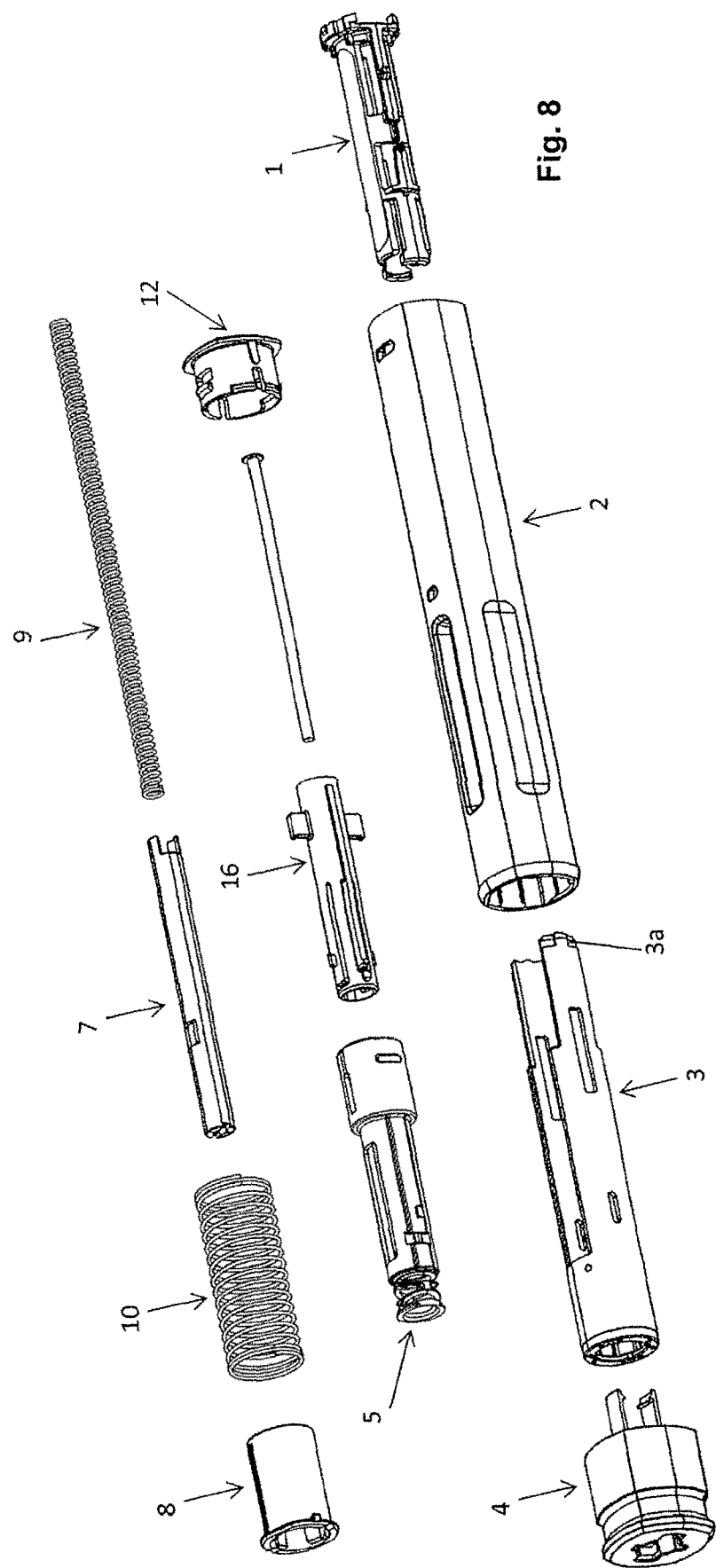

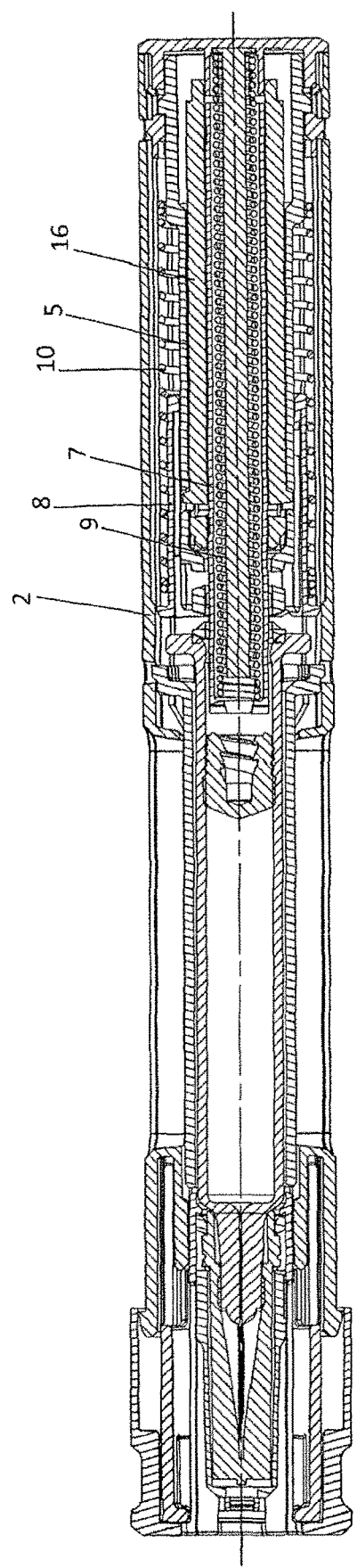
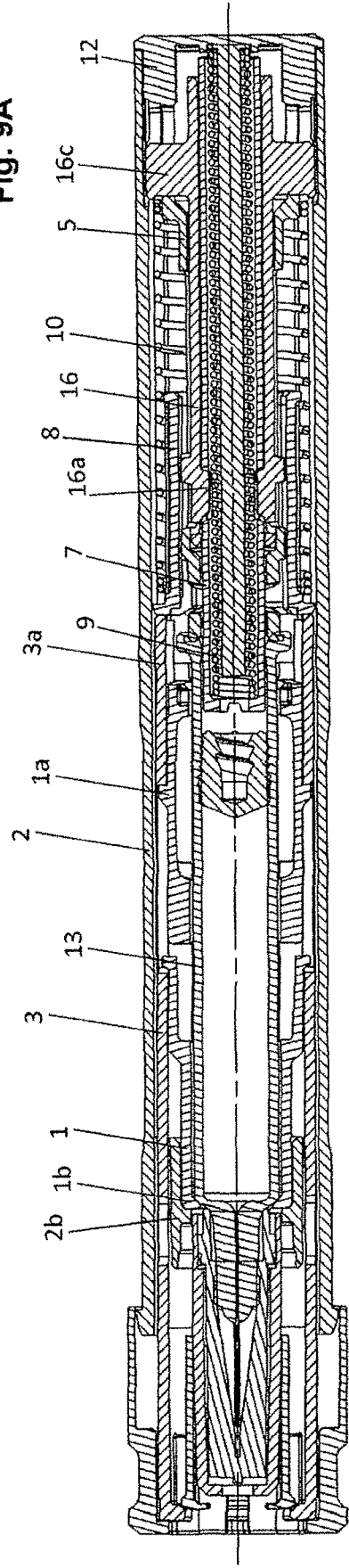
Fig. 9A
Fig. 9B

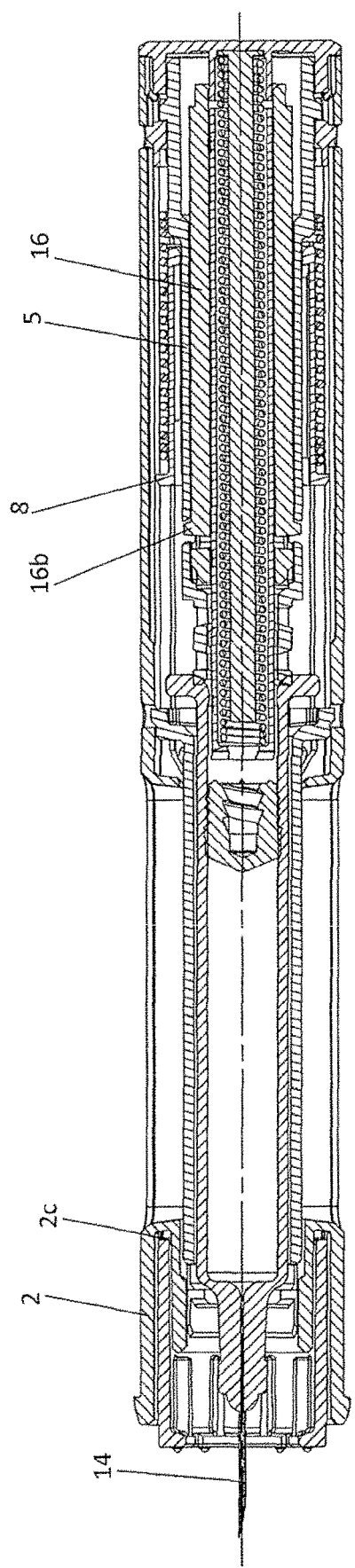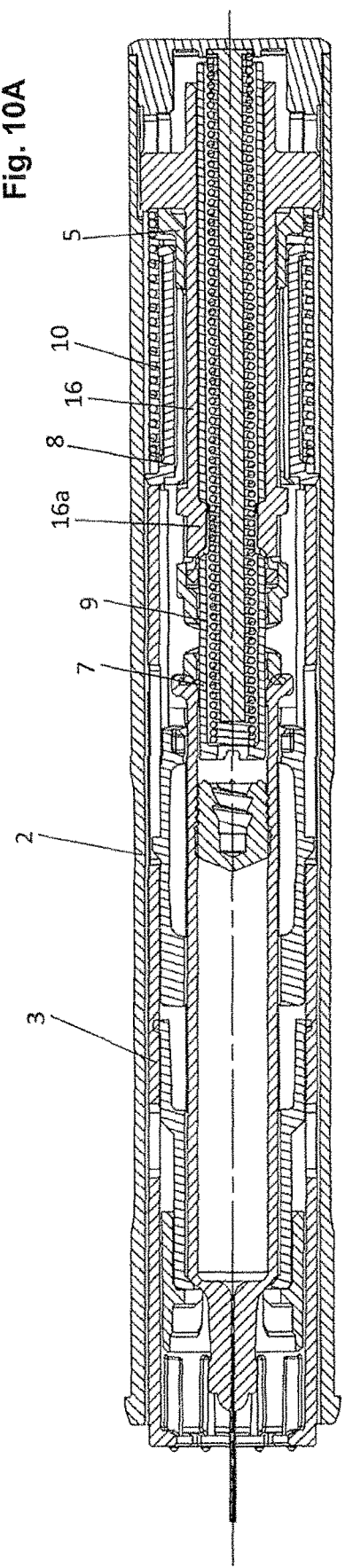

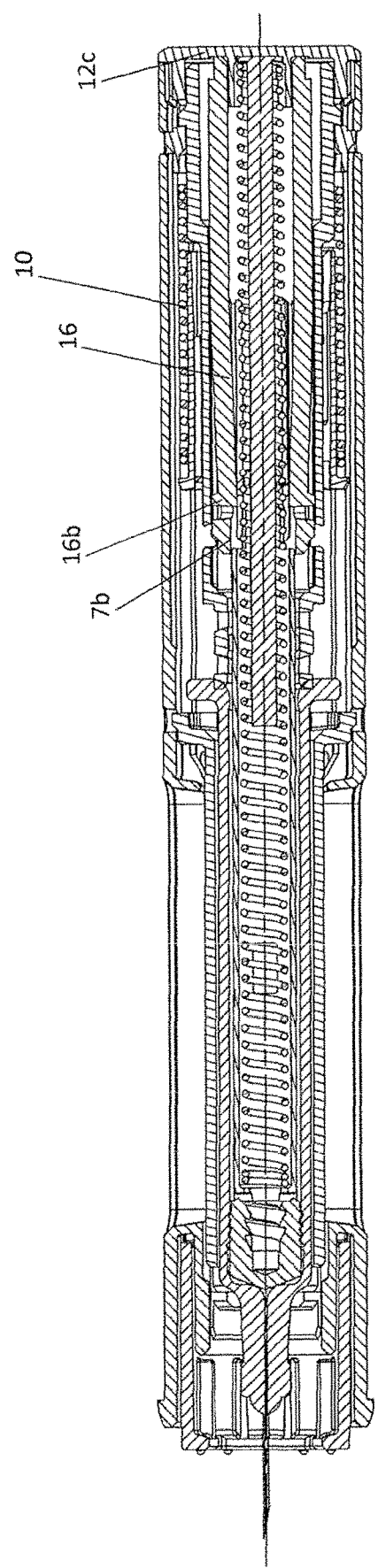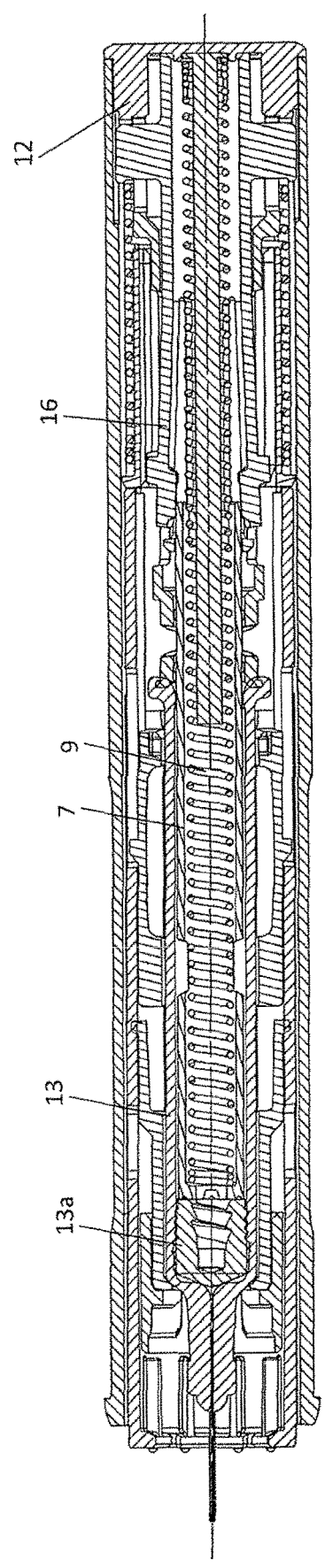

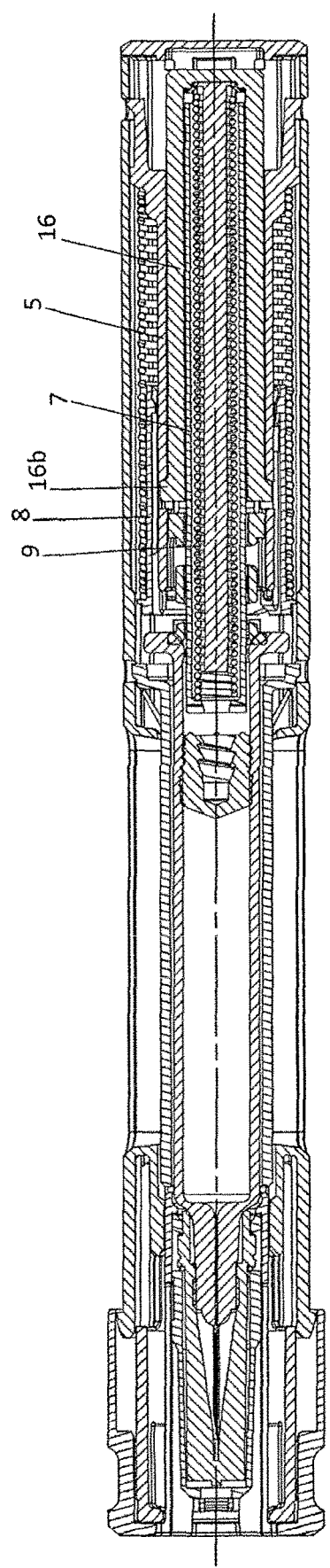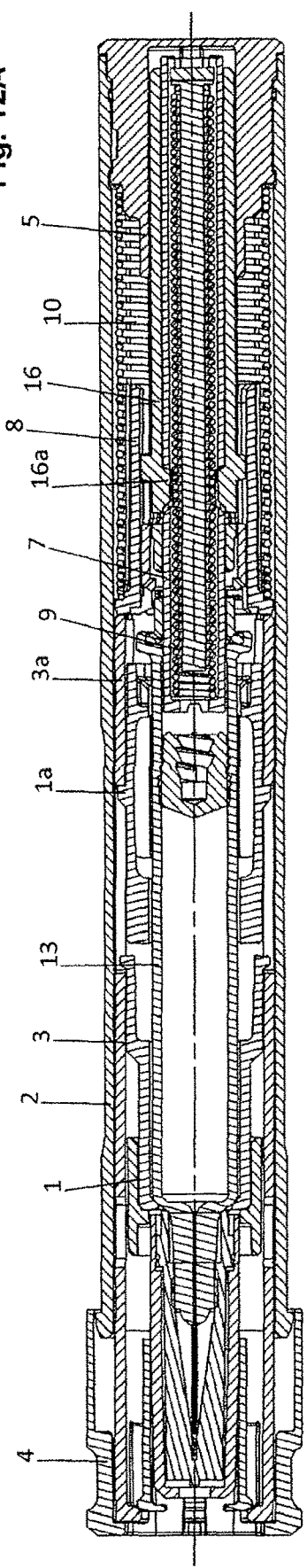

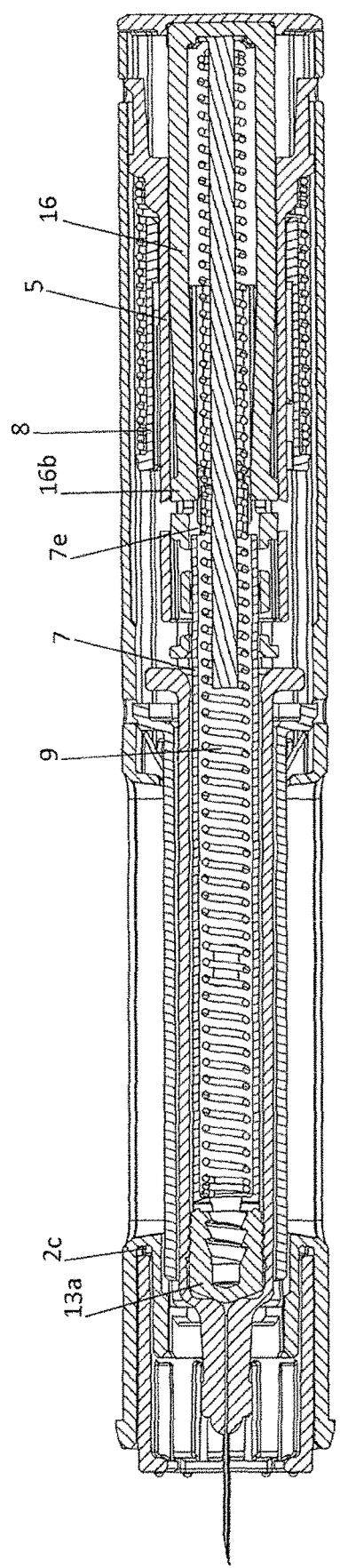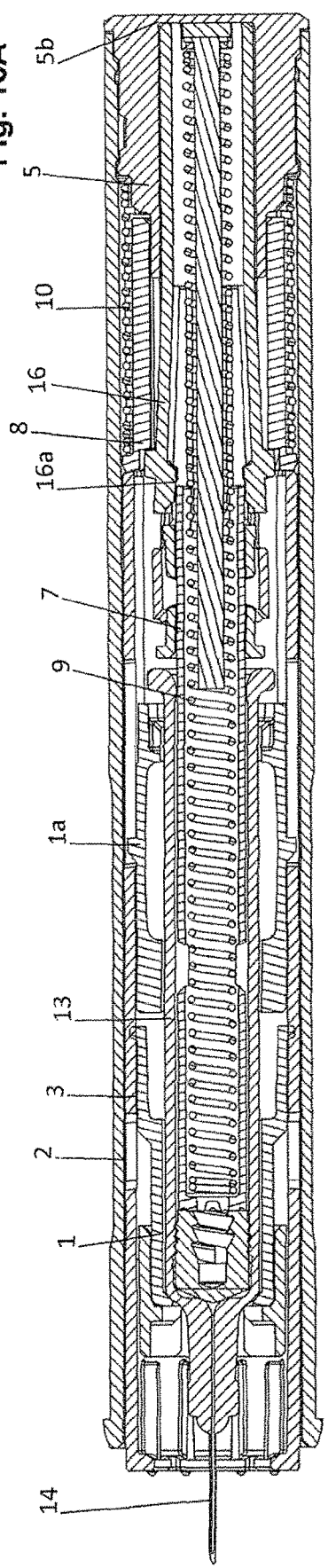

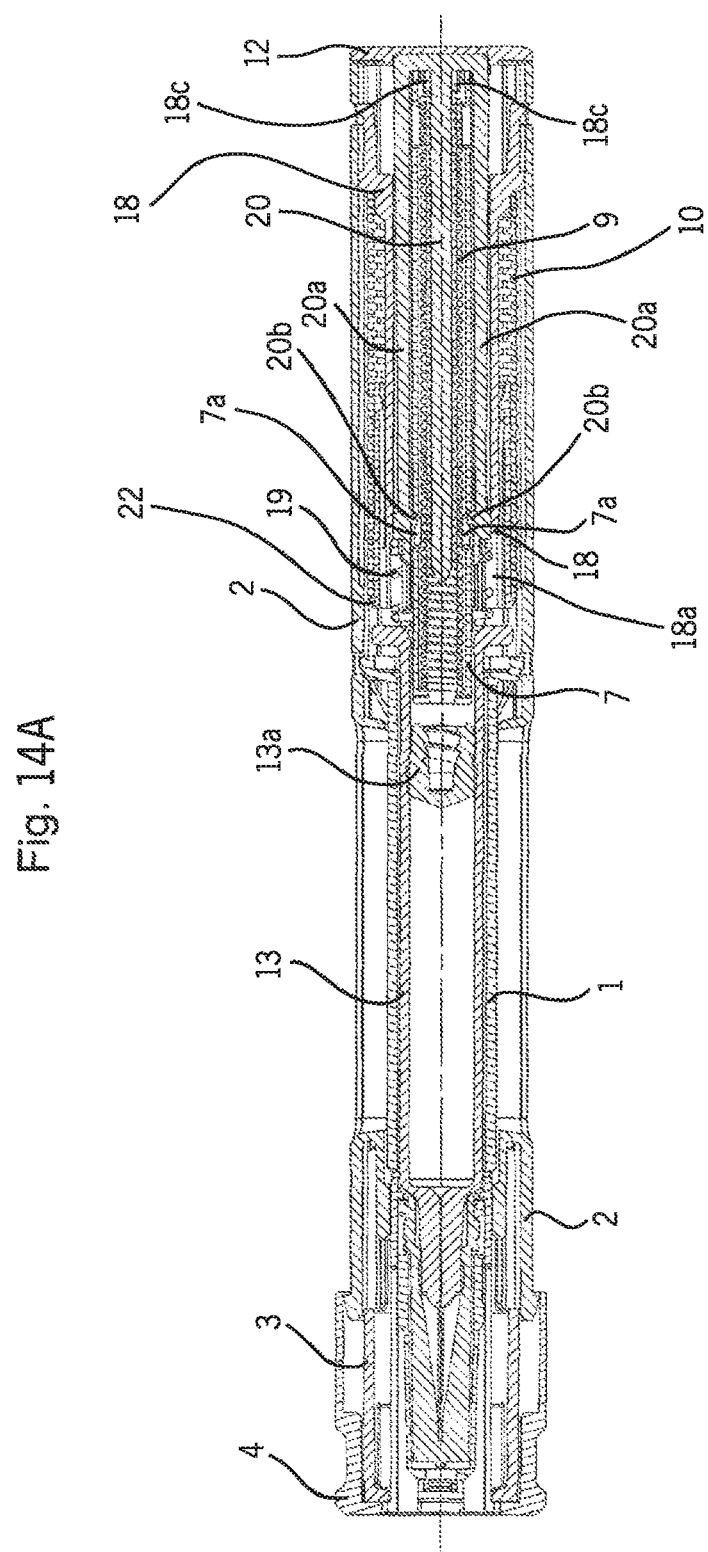

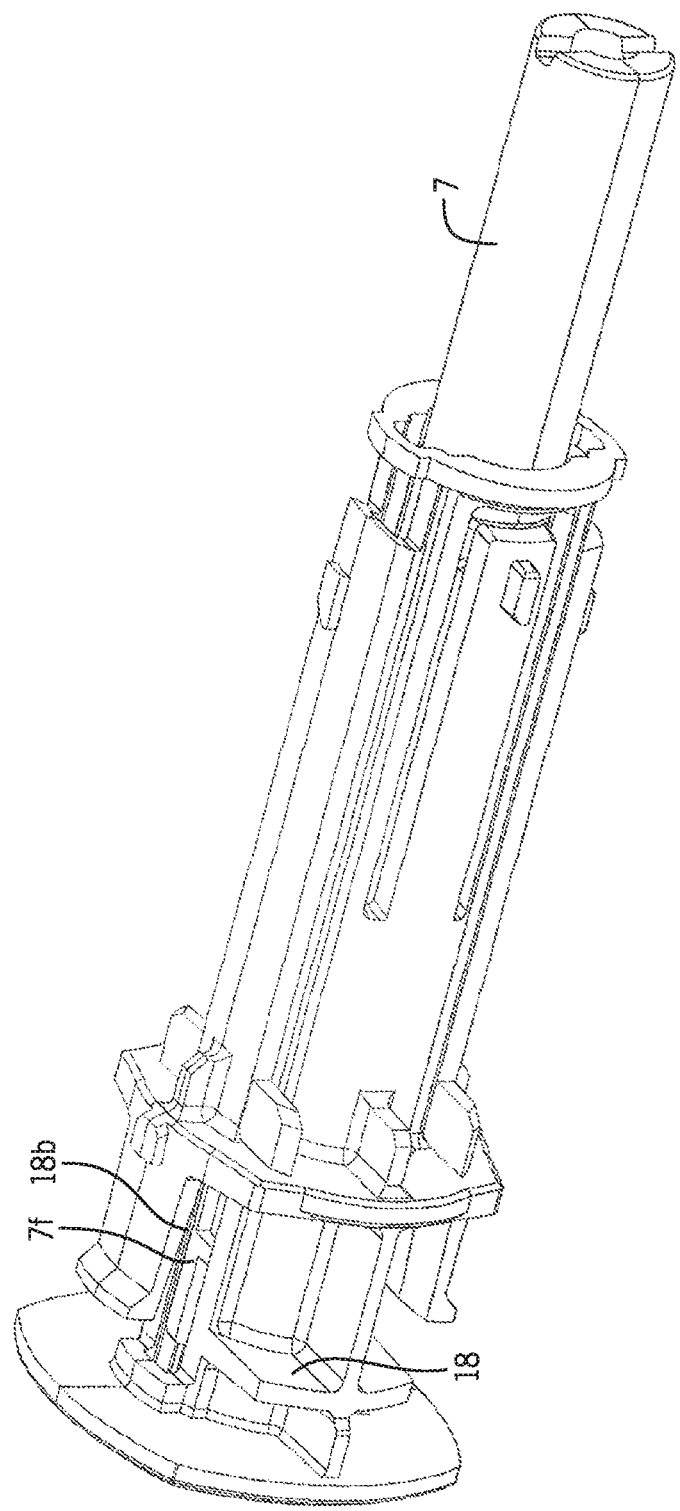

SUBSTANCE DISPENSING DEVICE WITH SIGNALING DEVICE

CROSS-REFERENCE TO RELATED APPLICATIONS

This application is a Continuation of International Patent Application No. PCT/CH2014/000034 filed Mar. 20, 2014, which claims priority to European Patent Application No. 13160614.7 filed Mar. 22, 2013, the entire contents of each are incorporated herein by reference.

TECHNICAL FIELD

The invention concerns a substance dispensing device, in particular, an injection device or an autoinjector, which features a signaling device to indicate, for example, optically, acoustically, and/or tactilely, when a substance has been released or a dispensing has taken place, completely or at least, to a predefined extent. A substance which can, for example, be dispensed automatically can be a fluid product or a medication, which may, for example, be liquid, paste-like or gel-like.

BACKGROUND

From WO 2011/123024 A1, a medication dispensing device with a drive device acting on a medication container so as to hold the drive device in a pretensioned state is known. An activation device interacts, with the holding device, to release the drive device from the pretensioned state. A feedback device can interact both with the holding device and with the drive device in order to generate a signal, which indicates that the medication has been completely ejected.

WO 94/11041 discloses an autoinjector with a first unit, which brings about an automatic needle penetration and which controls a second unit, which produces the release of the medication, so that the release of the medication is begun only if the needle penetration was carried out completely.

WO 2013/016832 A1 discloses an injection device for the automatic dispensing with a needle protective device, which can be displaced from a distal to a proximal position and from there, to a needle protective position and with a drive device that can move in a housing, which is driven to a dispensing position with a drive means, and with a rotating sleeve, which can be rotated from a first to a second position and has a first profile, which is in an operative connection with a second profile of the drive device. The drive device rotates through the first profile and the second profile, the rotating sleeve from the first to the second position.

SUMMARY

One object of the invention is to make available a substance dispensing device or an injection device, in which the user triggers an injection in a simple manner and can be informed by the device as to the correct functional course.

This object is attained by the device and method according to the independent claims, with advantageous further developments defined in the dependent claims.

A device in accordance with the invention for administering a substance is preferably an autoinjection device, which has an energy storage or a drive element, with which dispensing can be automatically carried out. Preferably, force or energy which is supplied or applied externally, for example, by a user, is not required. The energy storage or drive element advantageously stores the complete energy required for an automatic release of the substance. Such an energy storage or drive element can, for example, be a spring. This spring may be incorporated, into the injection device in an energy-storing state—that is, for example, compressed, pulled apart, or also twisted—and can release energy by an energy releasing process—that is, for example, by relaxation if the spring was incorporated compressed or twisted, or under torsional stress, or also by contraction if the spring was incorporated when pulled apart. The energy release advantageously takes place directly or indirectly—that is, via intermediate components—on a piston rod or pressure element which presses a stopper of a syringe and can push this stopper into the syringe.

Optionally, the energy storage element or another separate energy storage element can be provided, in order to automate the process of inserting a needle. The insertion process, however, can also be done manually—it can, for example, be undertaken by a user-without using energy stored in the injection device for that purpose.

The administration device has a release element, for example, a needle, by means of which the substance can be released. The needle is coupled with the container for the substance to be released in a known manner, so that, for example, upon displacing the aforementioned stopper, the substance passes through the needle and is released and injected at the distal front end of the substance.

A protective element is provided for the release element, for example, a sleeve which is to be pushed beyond the release element, which, for example, may be pushed axially, parallel to the longitudinal direction of a needle that serves as the release element. The protective element can surround the release element, for example, radially, prior to the release, and also protrude beyond the release element in distal direction, so that the release element is essentially or completely surrounded or covered by the protective element. The protective element thereby advantageously has a passage opening for the release element, through which the release element can leave the protective area of the protective element. The release element can be moved actively through the protective element and also the protective element can be removed actively from the release element—that is, for example, pushed back in a proximal direction—so as to release at least the distal area of the release element.

The protective element is coupled with a drive element which is or may be designed separately from the aforementioned, optionally provided drive elements or is designed, for example, as a second or third drive spring within an injection device. The protective element can be driven by this drive element. For example, the drive element can cause the protective element to be brought or pushed, over the release element once again after the substance has been released. Optionally, the drive element can also serve as a holding element, for example, in order to hold the protective element, in a protective position, over or around the release element before and/or after a substance release. The drive element can be incorporated, in a relaxed state or in a tensioned or loaded—that is, energy-containing or—storing, state in the injection device, wherein this energy can be used to drive the protective element. If the drive element is incorporated in the injection device in a state in which it does not store energy, or stores a small amount of energy, then during a functional course before driving the protective element, the drive element must be provided with energy by another element—that is, for example, by a user or one of the aforementioned other drive elements, for example, a tensioned dispensing spring.

A feedback device of the injection device can generate a signal if a predefined quantity or the entire quantity of the substance to be dispensed was released. The signal that is generated can be an acoustic signal—that is, for example, a "click" sound, which is generated if a moving element strikes another element. It is also possible for the acoustic signal to be, for example, a mechanically generated friction or scratching sound, when two elements are moved relative to one another. The signal can also be a tactile or haptic signal—that is, a signal which can be felt by a user. Such a signal can, for example, also be created by a stop of one element on another element, or a vibration or friction signal when two elements move, relative to one another. Furthermore, the signal can be a visual signal, such as a color signal or a color area of the feedback device, which is displaced, for example, in a certain area. For example, the feedback device can carry a signaling color, which is moved out of a visible area, or is moved into a visible area, in order to indicate that a substance release has not yet taken place, or also that it has been concluded.

According to the invention, the feedback device is coupled with the drive element with which the protective element is also coupled. For example, the feedback device is a stop element—that is, a pin or a sleeve—which is accelerated by a needle protective sleeve spring or is moved against a stop, wherein the needle protective sleeve spring acts on a needle protective element with pressure or exerts force on it, in order to bring or to hold in a protective position the needle protective element relative to the release element or to the needle.

The feedback element can, for example, strike the housing of the injection device and therefore move relative to it, wherein it is also possible that the feedback strikes any other part. Preferably, the feedback element is accelerated by the aforementioned drive element over a predefined distance, for example, straight or in a rotational movement, in order to produce a strike, at a certain speed, and thus a noticeable feedback signal.

The device according to the invention can have another separate, second feedback device, which, for example, signals the beginning of the substance release. It is conceivable that both feedback devices can also be implemented in one element.

As already mentioned, the administration device can also have a second, third, fourth, or other drive element or energy storage element, which, for example, makes energy available to bring about the substance release and/or energy for the carrying out of a needle penetration. This second or additional drive element is provided separately from the drive element which is coupled with the feedback device and can, for example, be functionally, completely separate from the feedback drive element. It is also possible that such an additional drive element releases or transfers energy to the feedback-drive element.

A modulation or dampening element can also be provided on the feedback element, by means of which the feedback coupling—that is, for example, a feedback sound or a tactile feedback signal—can be influenced or modified. For example, straps or stop surfaces or dampening means may be provided, which delay or decelerate an impact or strike of the feedback device on a surface or an impact part. Likewise, it is possible for a modulation element to increase the strike surface, in order to increase the signal strength that is to be generated.

The feedback element can preferably be held by a releasable holding device until the end of the substance release, so that, for example, the feedback element is triggered or released and, for example, is driven by a drive element only if the substance release is complete or has been carried out to a specific, previously defined extent—that is, for example, the piston rod was pushed to a stipulated dispensing point.

As mentioned above, the feedback coupling device can be a stop element which, for example, is accelerated or driven along a straight path, in order to strike, at the end, at a stopping place, and thus, create a feedback signal. It is also possible for the feedback device to be, for example, a rotating element, which, for example, carries out a rotational movement after the stipulated ending of the complete substance release and creates a rotational strike. For this, for example, a torsional moment of a used spring—that is, for example, a used needle protective spring or also an injection spring—can be used.

In accordance with another aspect, the invention refers to a method for the release of a substance from a device that is described above, wherein the substance is automatically released by means of a first drive element and a feedback signal for the signaling of the, for example, ended substance release by means of a feedback element, driven by a separate, second drive element, is generated. The drive elements are consequently separate devices or functional units—that is, for example, two separately provided springs which can, however, be coupled with one another, in order to transfer energy from a spring—such as, from a drive spring—to another spring—that is, for example, the feedback spring.

This transfer of energy or force can take place before, during, or after the substance release.

BRIEF DESCRIPTION OF THE DRAWINGS

FIGS. 3A and 3B are cross-sectional views of the injection device shown in FIG. 1, in the delivery state, rotated relative to one another by 90°.

FIGS. 3C to 3G is the execution of the radial inside of the locking sleeve (180° execution) for the illustration of the relative movement of the engaging cams of the mechanism holder and the click pin.

FIGS. 4A and 4B are cross-sectional views of the injection device shown in FIG. 1 in the inserted state, rotated by 90°, if the injection device is or was pressed onto the injection site.

FIGS. 4D to 4H are detailed views of the locking sleeve and the principle of the needle protective locking for the illustration of the relative movement of the intervening cams of the mechanism holder and the click pin.

FIGS. 5A and 5B are cross-sectional views of the injection device shown in FIG. 1, rotated relative to one another by 90°, before the beginning of the dispensing.

FIG. 8 is an exploded view of a second embodiment of an injection device.

FIGS. 9A and 9B are cross-sectional views of the injection device shown in FIG. 8 in the delivery state, rotated, relative to one another, by 90°.

FIGS. 10A and 10B are longitudinal cross-sectional views of the injection device shown in FIG. 8 in the inserted state, rotated, relative to one another, by 90°, if the injection device was pressed onto the injection site.

FIGS. 11A and 11B are cross-sectional views of the injection device shown in FIG. 8, rotated, relative to one another, by 90°, after the dispensing has been completed and the signaling of the end of the injection by the strike of the release sleeve on the end cap has taken place.

FIGS. 12A and 12B are cross-sectional views, rotated, relative to one another, by 90°, with regard to a third embodiment of an injection device in the delivery state.

FIGS. 13A and 13B are cross-sectional views of the injection device shown in FIGS. 12A and 12B, rotated, relative to one another, by 90°, with regard to the injection device after a completed penetration and dispensing movement and confirmation of the complete dispensing by striking the release sleeve on the bottom of the mechanism holder.

FIG. 14A shows a fourth embodiment of an injection device in the delivery state, in which the syringe spring makes available the energy for the end click (end-of-injection click).

FIG. 15A shows an embodiment of a functional unit of an end-click unit of an injection device in the delivery state, in which a rotational strike is generated by a torsional moment of the injection spring.

DETAILED DESCRIPTION

Figure 1:
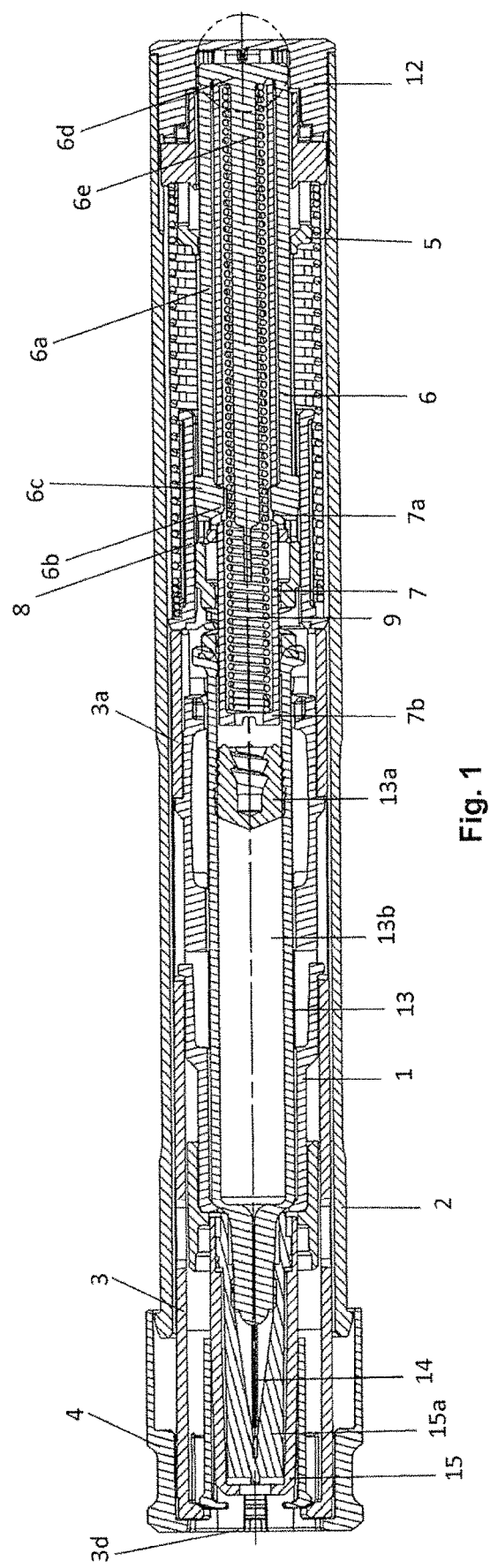
FIG. 1 is a cross-sectional view along a longitudinal axis of a first embodiment of an injection device for the illustration of the concept.
Figure 2:
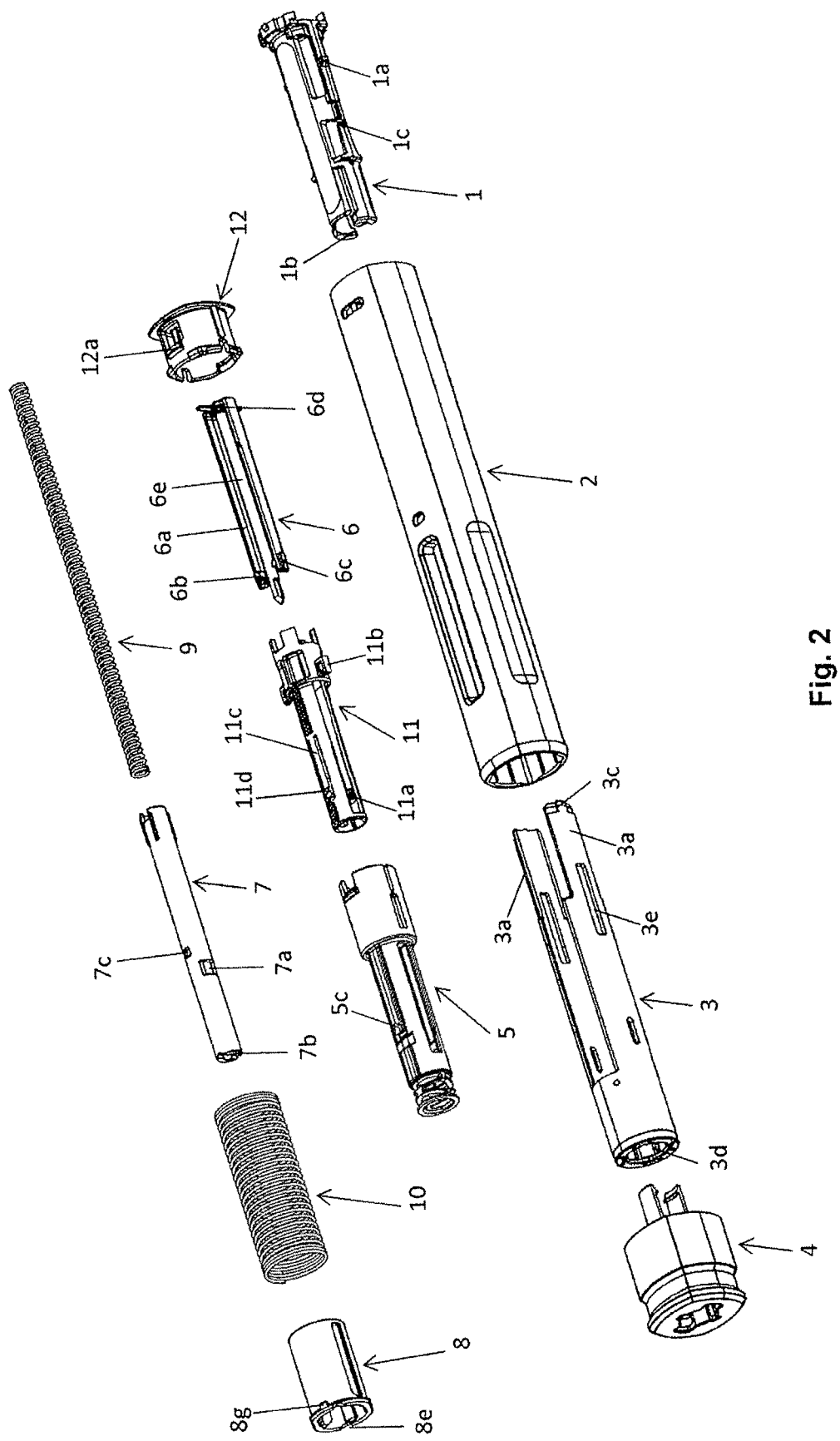
FIG. 2 is an exploded view of the injection device shown in FIG. 1.

FIGS. 1 and 2 show a concept of a first embodiment of an injection device, in accordance with the invention. The injection device comprises a sleeve-shaped housing 2, on which a syringe holder 1, a mechanism holder 5, and an end cap 12 are stationary in the housing—that is, do not move with respect to the housing 2. The syringe holder 1, the mechanism holder 5, and the end cap 12 can be locked in place, cemented, soldered, bolted, or snapped in the housing 2 or also they can be designed, as a whole, as a single piece with the housing 2. A preferably already prefilled syringe 13 can be taken in the syringe holder 1 and be held by it. The syringe 13 has a holding space 13b, which is limited by a stopper 13a which can be displaced along the longitudinal axis of the syringe 13, and in which a substance to be released is contained, which presses out from this space with the displacement of the stopper 13a in the distal longitudinal direction of the syringe 13 (in FIG. 1 to the left) and which can be released, in a known manner, by a needle 14 arranged on the front side of the syringe 13. The needle 14 is surrounded by a needle protective cap 15 in the starting state shown in FIG. 1, in which there is, for example, a needle protective element 15a, which may be elastic or made of rubber. The needle protective cap 15 can be removed, together with the rubber element 15a contained therein, by means of which the cap removal element 4 placed thereon, in order to release the needle 14, which, in the starting position shown, is also surrounded by the front side of a needle protective sleeve 3 that can be moved in and again out in the axial direction of the housing 2.

An injection spring 9 serving as an energy storage unit or drive means is pretensioned and in the starting state, is held between the piston rod 7 and the click pin 6, wherein the injection spring 9 is supported within the piston rod 7 and is surrounded by the piston rod 7, and the piston rod 7 presses on a distal bottom element 7b or is supported against it. In the proximal direction, the injection spring 9 is held by a proximal bottom or plate element 6d of a click pin 6 or is supported against it. The click pin 6 has a guide pin 6e in the axial direction, which is arranged, in the inserted state, within the injection spring 9 and is connected with the plate element 6d on the proximal end, from which the release snap arms 6a extend, running approximately parallel to the guide pin 6e, which are designed in an elastic manner or so they can be deformed—that is, they can be moved radially outwards or inwards. The inner cams 6b engage in indentations or openings 7a of the piston rod 7, so that, in this state, an axial displacement between the click pin 6 and the piston rod 7 is not possible by the force of the pretensioned injection spring 9. The spring package, consisting of the click pin 6, the piston rod 7, and the injection spring 9, can thus not be pressed apart. A radial release of the release snap arms 6a outwards is prevented by the axially displaceable sleeve 8, which is in the area of the outer cams 6c around the click pin 6; the outer cams 6c are opposite its inside or next to it.

The injection spring 9 is preferably a pressure spring or coiled spring, which preferably stores or can absorb at least the energy for the dispensing sequence and which is, as a tensioned spring, inserted into the injection device.

The needle protective device 3, which is designed as a sleeve-shaped element and is supported so it can be displaced relative to the housing 2, has a passage opening 3d on its distal front side, through which the needle 14 can pass or which moves back, in the axial direction, along the needle 14 or can be pushed into the housing 2. Extending in the axial direction are two opposite arms 3a, which are located, relative to the passage opening 3d, in the proximal direction.

FIGS. 3A and 3B are cross-sectional views of the injection device in the delivery state, rotated, relative to one another, by 90°. As already mentioned, the injection spring 9 is pretensioned between the piston rod 7 and the click pin 6. The piston rod 7 is held against the force of the injection spring 9, which exerts a force acting on the piston rod 7 in the distal direction, by the inner cams 6b of the release snap arms 6a of the click pin, as can be seen from FIG. 3B. The locking sleeve 8 prevents a movement of the cams 6b and the release snap arms 6a, directed radially outwards.

An end-click element 11 is pressed or held in the proximal direction by a needle protective sleeve spring 10, which presses on a ring-shaped radial expansion 11b of the end-click element 11.

On the opposite side, the needle protective sleeve spring 10 is supported on a flange 8g of the locking sleeve 8. The needle protective sleeve spring 10 can already be pretensioned, just like the injection spring 9, or it can be inserted, relaxed, into the injection device. The locking sleeve 8 is proximally shifted on the arms 3a of the needle protective sleeve 3, which is held against a displacement in a distal direction via proximal cams 1a of the spring holder 1, which is fixed in the housing; the cams protrude radially outwards and engage in recesses or passages of the arms 3a.

As shown in FIG. 3A, the end-click element 11, pressed or held proximally, holds the piston rod 7 in the proximal starting position shown by means of cams 11a, which are arranged on spring arms 11c, protruding radially inwards, and which engage in indentations or openings 7c of the piston rod 7; in the starting position, the distal front side of the piston rod 7 is at a distance from the proximal rear of the stopper 13a.

The end-click element 11 is in the starting or delivery state with its proximal front side on the plate-shaped bottom 12b of the end cap 12, which is stationary in the housing or is snapped on the housing 2 by means of the snaps 12a.

The syringe 13 inserted in the injection device is held, toward the front, in the syringe holder 1 by means of a shoulder support 1b or projections 1b of the syringe holder 1, which protrude radially inwards, and is secured by means of a ring or a housing tapering 2b in the housing 2. This ring or the housing tapering 2b prevents a radial release or escape of the syringe holder 1b. The syringe holder 1 is, on the front side, on ribs or projections 2e of the housing 2, which protrude radially inwards.

Cams 1c, which protrude radially outwards, on spring arms 1d of the syringe holder 1, which is stationary in the housing, engage in an axially running groove 3e of each arm 3a of the needle protective sleeve 3 and from the aforementioned radially protruding cams 1a, are as far in the axial direction as approximately the length of the axial groove 3e, so that the needle protective sleeve 3 is held against an axial displacement by the cams 1a and 1c, which, at a distance axially from one another, engage in the axial groove 3e, wherein the cams 1c provided on the spring arms 1d, move radially inwards with an application of a relatively small pressing force on the needle protective sleeve 3 and make possible a proximal pushing of the needle protective sleeve 3 into the housing.

FIGS. 3C-3G show an inner execution of 180°—that is, a half of the locking sleeve 8, wherein areas protruding radially inwards are shown crosshatched. The positions of the locking sleeve 8 are thereby explained in connection with the movements of the needle protective sleeve 3.

The locking sleeve 8 is shown in the starting state of the needle protection in FIG. 3C. The guide areas or grooves of the locking sleeve 8 located between the crosshatched areas, enable an intervention of a cam 6c of the click pin 6, directed radially outwards. Furthermore, a cam 5c of the mechanism holder 5, protruding outwards in the radial direction, meshes into an axially running groove 8a, which is provided on the radial inside of the locking sleeve 8, and is engaged with it, so that a rotation of the locking sleeve 8, relative to the mechanism holder 5, which is stationary in the housing, is prevented. In the position shown, the locking sleeve 8 can, however, be pushed in the axial direction.

Before the beginning of use of the injection device, the needle 14 must be released, and to do this, the cap removal element 4 is removed, in the distal direction, from the distal front side of the injection device. As one can see from FIG. 3A, the snap hooks 4a of the cap removal element 4 snap in behind the rear edge of the needle protective cap 15. Ribs 2f of the housing 2 which are provided on the radial outer side of the snap hooks 4a and are next to these prevent a release or escape of these snap hooks 4a, so that by a pulling on the cap removal element 4, it is possible to remove the needle protective cap 15 in the distal direction. The elastic or rubber needle protection 15a, fastened within the needle protective cap 15, is thereby also removed together with the needle protective cap 15, so that the needle 14 is released. The cap removal element 4 is held on the needle protective sleeve 3 by means of a snap element 4b, which engages behind a radially protruding snap holder 3b. Upon removal of the cap removal element 4, a force which can overcome the snap holder 3b, 4b must be applied.

After the removal of the cap removal element 4, together with the needle protective cap 15, the needle 14 is released, but is still surrounded by the distal sleeve area of the needle protective sleeve 3, which projects also in the distal direction beyond the tip of the needle 14, so that the needle 14 is still protected by the front or distal part of the needle protective sleeve 3.

If the injection device, situated in the ready-to-use state after the removal of the cap removal element 4, with its distal front side—that is, the distal front area of the needle protective sleeve 3—is pressed onto a puncture site, then by this pressure which is usually applied onto the housing 2 by a user holding the housing 2, the needle protective sleeve 3 is displaced, in the proximal, axial direction, into the housing 2, wherein the needle 14, which is stationary relative to the housing 2, is released and pierces the puncture site.

This state is shown in the cross-sectional views of FIGS. 4A and 4B, which are rotated relative to one another by 90°. With an appropriate pressure exerted on the housing 2 in the distal direction, the needle protective sleeve 3 is inserted through the contact surface surrounding the puncture site into the housing 2, to the stop 2c limiting the insertion of the needle protective sleeve 3, which takes place simultaneously with the puncture of the needle 14 into the injection site.

By the insertion of the needle protective sleeve 3, as shown in FIGS. 3B and 4B, the locking sleeve 8, next to the proximal end of the arms 3a of the needle protective sleeve 3, is likewise pushed in the proximal direction, relative to the housing 2, wherein the needle protective sleeve spring 10, which is supported between the aforementioned contact surfaces of the locking sleeve 8 and the end-click element 11, is compressed or tensed.

Figure 3E:
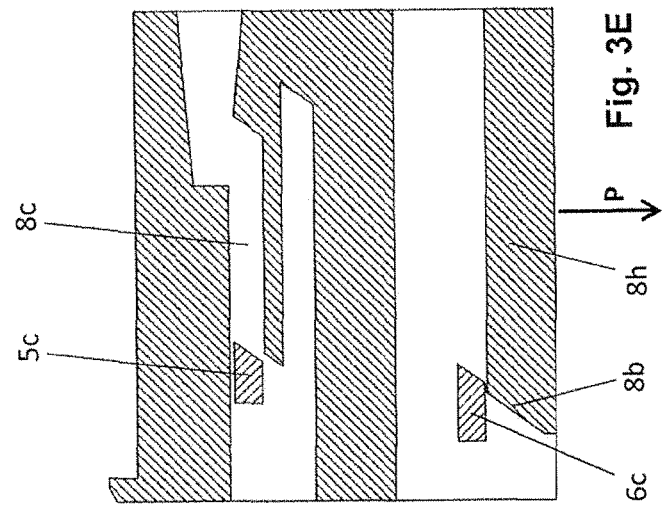
Figure 4E:
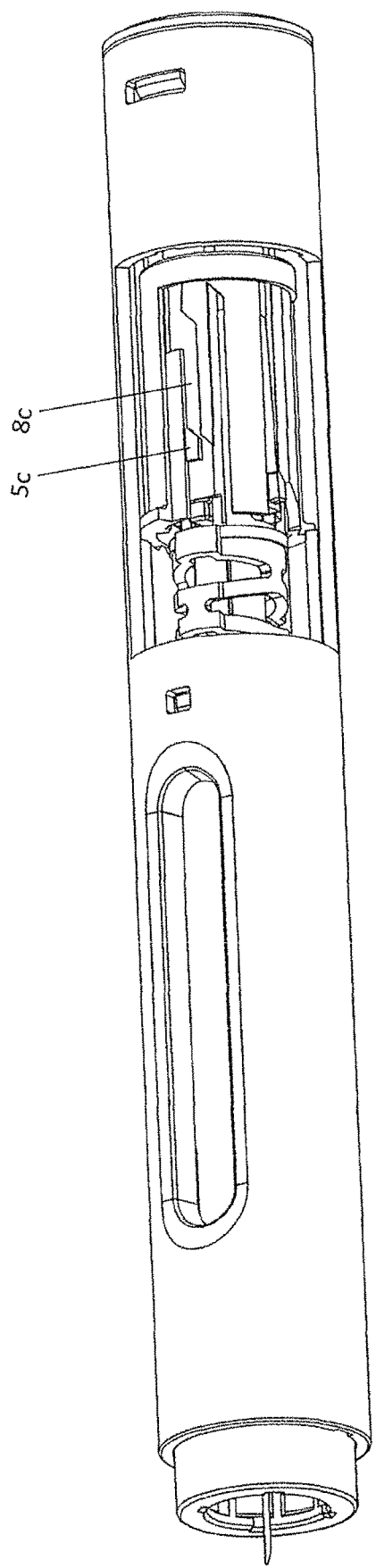
Figure 3G:
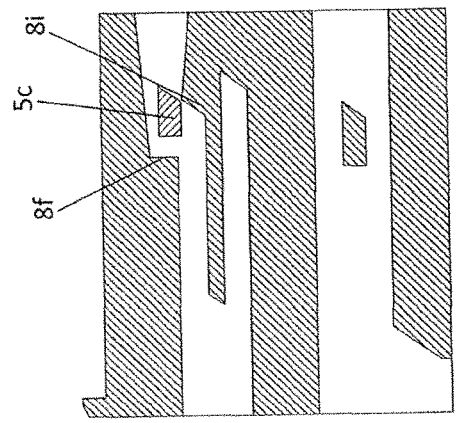
Figure 4G:
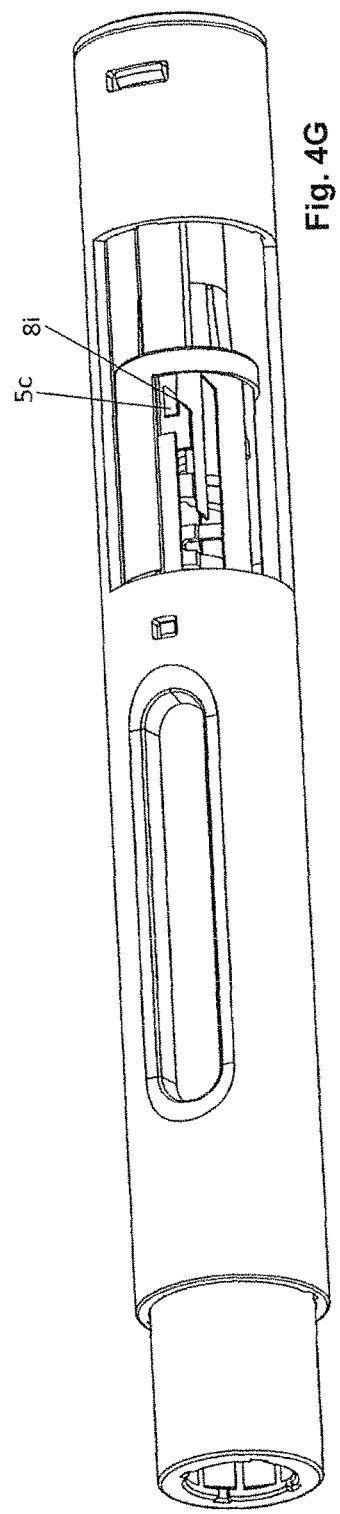

In the starting position shown in FIG. 3C, the cam 6c, protruding radially outwards and lying on an elastic release snap arm 6a of the click pin 6, is still outside a guide area on the radial inside of the locking sleeve 8 and only after the puncture, is it moved in the axial direction, relative to the locking sleeve 8, by an axial displacement of the locking sleeve 8, relative to the housing 2, into an engagement area, as shown in FIG. 3D and in FIG. 4D, in which the cam 6c, with a front bevel in the axial direction, is next to a bevel 8b of the bar 8h. Since, in this state, a force acting in the distal direction (in FIG. 3E, to the left) is exerted by the needle protective sleeve spring 10 on the locking sleeve 8, the system—present on the bevel 8b—on the cam 6c of the click pin 6, which is held against an axial displacement by the pressing force of the injection spring 9, leads to a rotation operation of the locking sleeve 8 in the direction shown by the arrow P. By the rotation of the locking sleeve 8, relative to the housing 2, the locking sleeve 8 is also twisted relative to the cam 5c of the mechanism holder 5, so that the cam 5c either engages in the axially running locking path 8c, shown in FIG. 3E and FIG. 4E, or is about to engage.

If the housing 2 of the injection device is pressed onto the injection site to the extent that the needle protective sleeve 3 is almost completely pushed or is completely pushed into the housing 2, as shown in FIGS. 4A and 4B, the automatic injection is released. The locking sleeve 8 is thereby axially pushed in the proximal direction, by the adjacent arms 3a of the needle protective sleeve 3, within the housing, to such an extent that the release snaps 6a of the click pin 6 are released by the locking sleeve 8, which has been pushed away and is no longer lying around the outer cams 6c, wherein the release snap arms 6a can move radially outwards. Since the piston rod 7 is acted on with a force, by the injection spring 9, in a distal direction, relative to the housing, the inner cams 6b are pressed out from their engagement in the openings 7a of the piston rod 7, which is supported by the bevels 6f and 7d, shown in FIG. 5B.

The release snap arms 6a of the click pin 6, which are correspondingly pressed radially outwards, are shown in FIG. 5B. In this way, the piston rod 7 is released and driven by the force of the pretensioned injection spring 9, can move, relative to the housing 2, within the housing in the distal direction onto the stopper 13a. Moreover, the click pin 6 is also released and pressed by the force of the injection spring 9 axially, within the housing 2, in the proximal direction, strikes, to the proximal front surface of the pin 6, the distal bottom surface of the end cap 12, as shown in FIGS. 5A and 5B. A start signal or start click is produced by the striking of the click pin 6 on the end cap 12. Dampening elements can be placed between the end cap 12 and the click pin 6, wherein the striking or impact of the click pin 6 can be delayed or decelerated and thus, the start signal can be modified. For the purpose, as shown in FIGS. 3A and 3B, for example, a squeeze rib 12c and a counter-rib 12c', which is, at an angle, opposite the squeeze rib 12c, can be placed between the end cap 12 and the click pin 6. Furthermore, additional dampening straps or snaps 12d and opposing dampening ribs 12d' can be placed.

As already described, the needle protective locking is activated (FIG. 4D) by the pressing of the snap arms 6a.

FIGS. 5A and 5B show cross-sectional views of the injection device rotated relative to one another by 90°, after the start click was carried out, which signals acoustically and tactilely the beginning of the injection, and the activation of the signal, described below, for the indication of the end of the injection (end-of-injection click).

The piston rod 7 is moved by the force of the relaxing injection spring 9 in the distal direction and comes to a stop at the stopper 13a, on which the piston rod 7 exerts a force acting in the distal direction by the injection spring 9, which is proximally supported, wherein the stopper 13a is pushed into the syringe 13, in order to displace the substance contained in the syringe 13, which is released or injected by the inserted needle 14.

As shown in FIG. 4A, the piston rod 7 is still connected with the end-click element 11 by means of the cams 11a, which engage in corresponding indentations or recesses of the piston rod 7, before the displacement for the impingement on the proximal side of the stopper 13a. This engagement is secured by the mechanism holder 5, surrounding the click element arms 11c, which prevents the click element arms 11c from moving radially outwards and thus can trigger the engagement in the piston rod 7. If the piston rod 7 is pushed in the distal direction to such an extent that the outer cams 11d of the click element arms 11c can engage in the release openings of the mechanism holder 5, as shown in FIG. 5A, then the click element arms 11c are pressed to the extent that they do not change with the piston rod 7, so that the displacement-secure coupling with the piston rod 7 is triggered. In this way, the end-click element 11 is held back. Since the protective sleeve spring 10 is supported, at its proximal end, against the end-click element 11, the needle protective sleeve spring 10 is tensioned by the displacement of the end-click element 11 in the distal direction, as can be seen from FIGS. 5A and 5B. Thus, there is an energy transfer from the relaxing injection spring 9 to the tensioning needle protective sleeve spring 10.

Figure 6A:
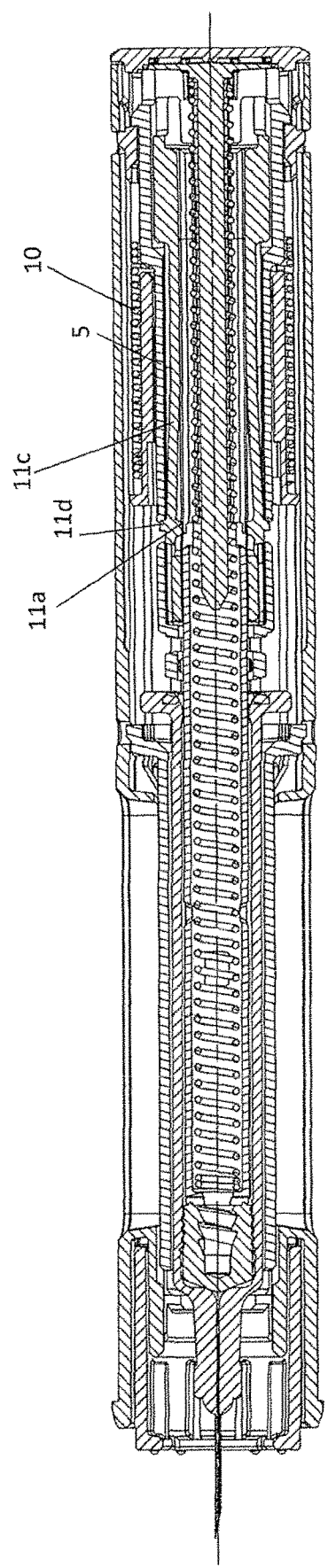
FIGS. 6A and 6B are cross-sectional views of the injection device shown in FIG. 1, rotated, relative to one another, by 90° after the dispensing has been completed.
Figure 6B:
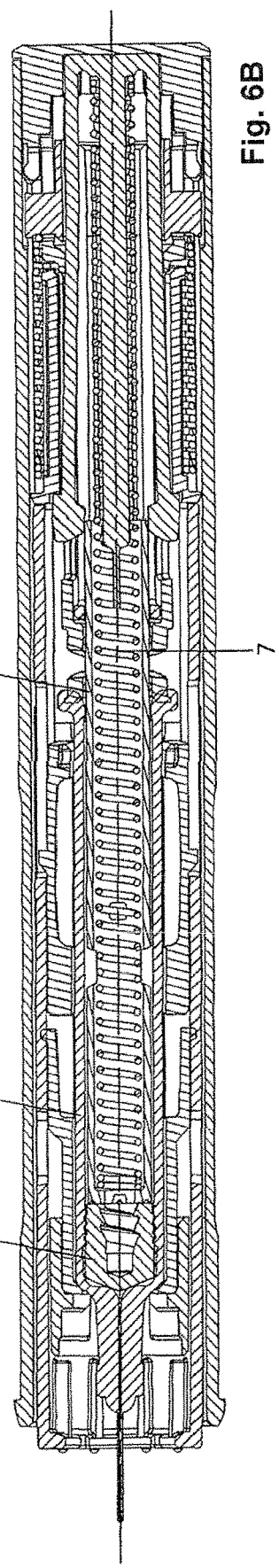

FIGS. 6A and 6B show longitudinal cross-sectional views of the injection device rotated relative to one another by 90°, after the dispensing of the substance. The piston rod 7, which is no longer held back, was thereby pushed into the syringe 13 by the force of the injection spring 9, wherein the stopper 13a was moved in a distal direction until it was at the end of the glass body and the substance was thus completely dispensed or released.

Figure 7A:
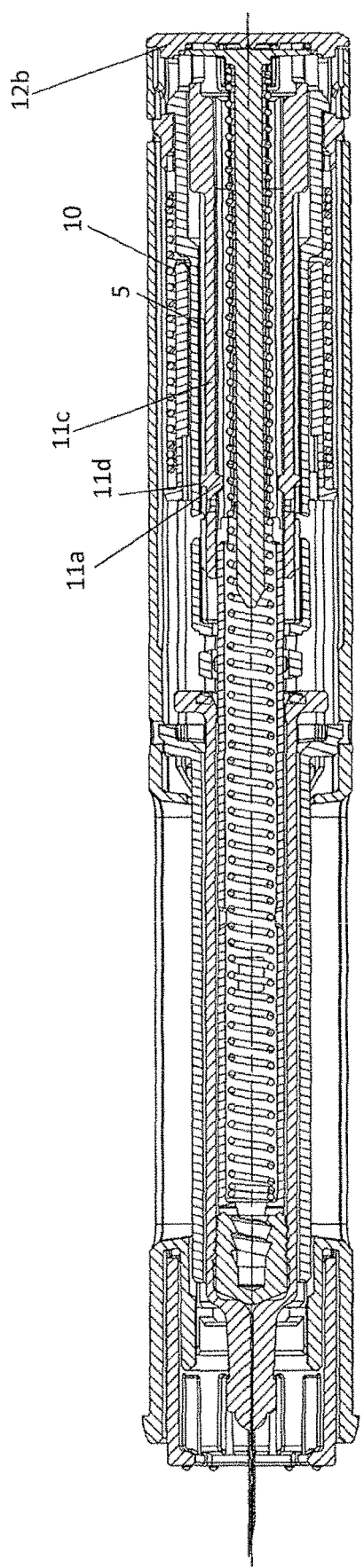
FIGS. 7A and 7B are cross-sectional views of the injection device shown in FIG. 1, rotated, relative to one another, by 90° after the dispensing has been completed and the strike of a click element, confirming this completed dispensing.

The one movement of the cams 11a, directed radially inwards, was pushed onto the piston rod 7, hindering the click element arms 11c, which is placed on the inner cams 11a of the end-click element 11 in the state shown in FIGS. 5A and 5B, in the distal direction, after the dispensing, as shown in FIG. 6A, to such an extent in the distal direction that the click element arms 11c are again released. Since the end-click element 11 is impinged by pressure by the needle protective sleeve spring 10, in the proximal direction, the holding engagement of the click element arms 11c is detached by means of the outer cams 11d in the mechanism holder 5 and releases the end-click element 11, as shown in FIG. 7A. The end-click element 11 is moved in the proximal direction after release by the needle protective sleeve spring 10, until it strikes the bottom 12b of the end cap 12 and causes an end click. This end click can be heard and can be perceived tactilely also by a user, in order to thus signal the end of the injection. The end click is consequently not brought about by the injection spring 9.

Figure 7B:
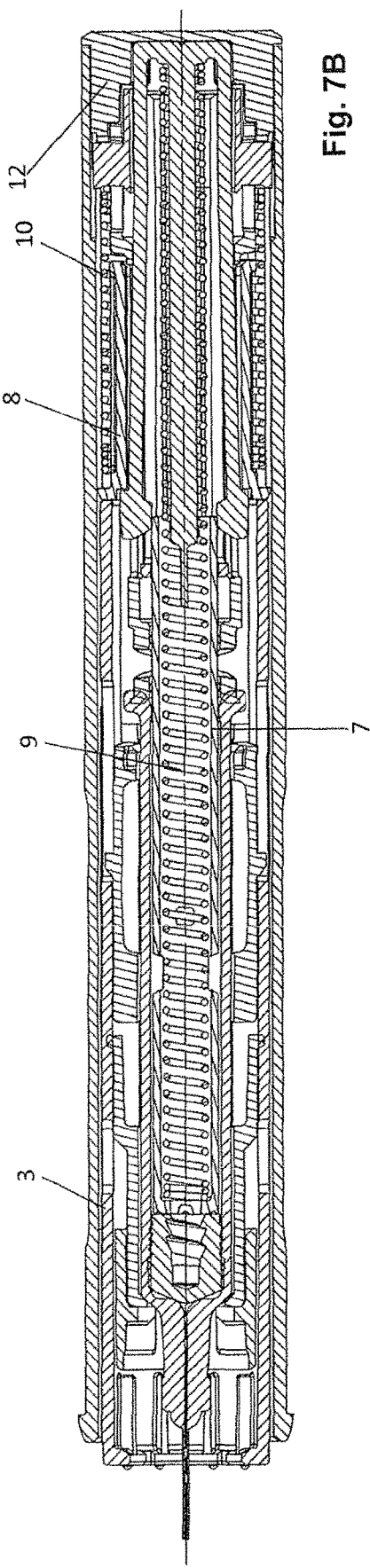

FIGS. 7A and 7b show longitudinal cross-sectional views of the injection device rotated relative to one another by 90° with an end click or after an end click has been carried out. If the injection device is removed from the injection site after a dispensing has been carried out, then the needle protective sleeve 3 is moved together with the locking sleeve 8 pressing on it, both of which are acted on by the needle protective sleeve spring 10, in the distal direction, with a force to the front—that is, relative to the housing 2, axially in the distal direction.

Figure 4H:
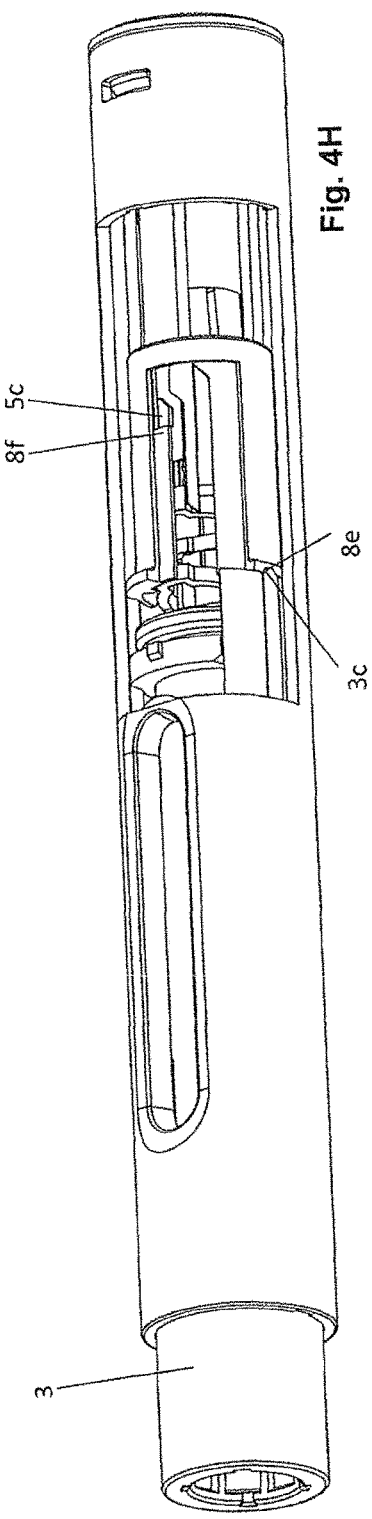

By the force of the needle protective sleeve spring 10, the locking sleeve 8 is pushed axially in the distal direction (in FIG. 3E, to the left, and FIG. 4E), wherein this axial displacement triggers a rotation of the locking sleeve 8 by means of the bevels 8b and the cam 6c and, in this way, the cam 5c is guided to engage with the axially running groove 8c and the locking sleeve 8 is thus secured with respect to twisting during this displacement. If the locking sleeve 8 has been pushed to such an extent that the cam 5c comes to a stop at the bevel 8i on the proximal end of the groove 8c, as shown in FIGS. 3F and 4F, then further pressure exerted on the locking sleeve 8, in the distal direction, leads to a further rotation of the locking sleeve 8 in the direction shown by the arrow P (FIGS. 3F, 4F and 3G, 4G), wherein the cam 5c lines up at the step 8f of the locking sleeve 8 and thus, prevents a pushing back of the locking sleeve 8 and the needle protective sleeve in the proximal direction (in FIG. 4H, to the right).

A centering cam 3c, provided on an individual arm 3a of the needle protective sleeve 3 engages, in this state, in a centering groove 8e of the locking sleeve 8 and thus prevents the locking sleeve 8 from rotating back. Thus, in this state, the needle protective sleeve 3 is pushed out beyond the needle 14 and secured against a pushing back by the cam 5c which lines up at the step 8f of the locking path 8c.

FIG. 8 shows an exploded view of a second embodiment of an injection device.

FIGS. 9A and 9B show longitudinal cross-sectional views rotated relative to one another, by 90°, in the delivery state. The injection spring 9 is pretensioned between the piston rod 7 and the end cap 12. A release sleeve 16 lies, toward the front via ribs 16c, on the mechanism holder 5. The mechanism holder 5 and the end cap 12 are firmly connected with one another. The piston rod 7 is held, in the distal direction, by a triggering snaps 16a of the release sleeve 16 and is secured by means of the locking sleeve 8. A cam 5c of the mechanism holder 5 engages with an axially running groove 8a of the locking sleeve 8 and prevents a twisting of the locking sleeve 8, relative to the mechanism holder 5.

The needle protective sleeve spring 10 is pretensioned between the locking sleeve 8 and the release sleeve 16. The mechanism holder 5 and the end cap 12 are stationary in the housing and are connected with the housing 2, for example, with snaps or by locking in place.

The locking sleeve 8 lies on straps or arms 3a of the needle protective sleeve 3, which is held, toward the front via a cam 1a, on the syringe holder 1. The release sleeve 16 is held, toward the back via the triggering snaps 16a of the release sleeve 16, secured by the locking sleeve 8, on the piston rod 7.

Just as described in the first embodiment, the syringe 13 is secured by means of a shoulder support 1b and by means of a ring or a housing tapering 2b.

The removal of the needle protective cap 4 is likewise carried out as described in the first embodiment example.

FIGS. 10A and 10B show longitudinal cross-sectional views of the injection device, rotated, relative to one another, by 90°, in the pierced state, if the injection device is pressed on the injection site. The needle protective sleeve 3 is pressed into the housing 2 to the stop 2c, while the needle is inserted into the injection site. The needle protective sleeve 3 displaces the locking sleeve 8, relative to the mechanism holder 5 and the release sleeve 16, wherein the needle protective sleeve spring 10 is tensed or compressed.

The injection is triggered by the complete insertion of the needle protective sleeve 3 into the housing 2. The locking sleeve 8 is thereby pushed in the proximal direction (in FIG. 10, to the right), relative to the housing 2, the mechanism holder 5, and the release sleeve 16, wherein the triggering snaps 16a are released. By the force of the injection spring 9, the triggering snaps 16a are pressed and free in a distal direction to the front, against the movement of the piston rod 7. The release sleeve 16 is then held toward the rear, on the mechanism holder 5, via the snap arms 16b.

FIGS. 11A and 11B show longitudinal cross-sectional views of the injection device rotated relative to one another by 90° after the dispensing and after the click for the signaling of the end of the injection has been carried out (end-of-injection click). The piston rod 7 was thereby moved in the distal direction by the force of the injection spring 9, wherein the piston rod presses on the stopper 13a and moves it in the distal direction until it is at the end of the glass body of the syringe 13. At its proximal end, the piston rod 7 has a slit 7b, wherein the snap arms 16b of the release sleeve at the end of the injection are released and the blocking of the release sleeve 16 is lifted toward the rear.

As soon as the snap arms 16b of the release sleeve 16 are released by the slit 7b of the piston rod 7, the snap arms 16b are deflected, wherein the release sleeve 16 is moved to the rear by the force of the needle protective sleeve spring 10 and strikes the bottom 12c of the end cap 12 and produces the end click.

The needle protective locking takes place in the same manner as described in the first embodiment example, wherein the deflected triggering arms are located on the release sleeve 16 and not on the click pin 6, so that in this regard, reference is made to the above description.

FIGS. 12A and 12B show longitudinal cross-sectional views of a third embodiment of an injection device rotated relative to one another by 90° in the delivery state. The injection spring 9 is pretensioned between the piston rod 7 and the release sleeve 16. The release sleeve 16 is held by the snap arms 16b on the mechanism holder 5 and secured by means of the piston rod 7. The piston rod 7 is held toward the front by the triggering snaps 16a and secured by means of the locking sleeve 8. The cam 5c of the mechanism holder 5 engages with the axially running groove 8a of the locking sleeve 8 and prevents a twisting of the locking sleeve 8, relative to the mechanism holder 5, which is stationary in the housing.

The needle protective sleeve spring 10 is pretensioned between the locking sleeve 8 and the mechanism holder 5. The mechanism holder 5 is locked by snaps with the housing 2. The locking sleeve 8 lies on the arms 3a of the needle protective sleeve 3, which is held toward the front on the syringe holder 1 via the cams 1a.

As described in the embodiment above, the syringe 13 is supported in the syringe holder 1 and the housing 2.

The removal of the cap removal element 4 for the removal of the needle protective cap 15 takes place as described above.

FIGS. 13A and 13B show longitudinal cross-sectional views of the injection device rotated relative to one another by 90° which was pressed on the injection site; the contents of the syringe were dispensed and signaling of the end of the injection was carried out.

First the needle 14 is inserted. The needle protective sleeve 3 is pressed into the housing 2 to the stop 2c. The needle protective sleeve 3 displaces the locking sleeve 8 relative to the mechanism holder 5 and the release sleeve 16, wherein the needle protective sleeve spring 10 is tensed.

The injection is triggered by the complete pushing in of the needle protective sleeve 3 into the housing 2. The locking sleeve 8 is thereby pushed in the proximal direction, relative to the housing 2, the mechanism holder 5, and the release sleeve 16, wherein the triggering snaps 16a are released. By the force of the injection spring 9, the triggering snaps 16a are pressed and freed to the front, against the movement of the piston rod 7.

By the force of the injection spring 9, the piston rod 7 was moved in the distal direction, wherein the piston rod 7 presses on the stopper 13a and moves it to such an extent in the distal direction that it is next to the end of the glass body of the syringe 13. On its proximal end, the piston rod 7 has a slit 7c, wherein the snap arms 16b of the release sleeve 16 are released at the end of the injection and the blocking of the release sleeve 16 is lifted in the proximal direction or toward the rear.

As soon as the snap arms 16b of the release sleeve 16 are released by the slit 7c of the piston rod 7, the snap arms 16b are deflected, wherein the release sleeve 16 is moved in the proximal direction by the force of the injection spring 9 and strikes the bottom 5b of the mechanism holder 5 and produces the end click.

The needle protective locking takes place in the same manner as described in the second embodiment example.

FIG. 14a shows a longitudinal cross-sectional view of another embodiment of an injection device in the delivery state, in which the injection spring 9 lies, on its distal end, on the inside of the piston rod 7. On its proximal end, the injection spring 9 is next to a holding sleeve 18, which is stationary in the housing, which surrounds a click pin 20 and radially, on a proximal site with engagement arms 18c, through openings of piston rod 7, engages with them. The click pin 20, provided for the generation of the end click, is pressed, in the proximal direction (in FIG. 14A, to the right), on the holding sleeve 18, via a syringe spring 19, which presses on distal end surfaces of click pin arms 20A, wherein the end cap 12 can be a part of the holding sleeve 18. The syringe spring 19 is supported, in the proximal direction, on the arms 20a of the click pin 20 and presses, in the distal direction, on the syringe 13, in order support it securely in the syringe holder 1 by the acting pressure produced in the distal direction. The arms 20a of the click pin 20 are engaged in openings 7a of the piston rod 7 by means of cams 20b that protrude radially inwards and can be entrained in a distally directed movement of the piston rod 7, so that the piston rod 7 first entrains the click pin 20 in a distal movement from the delivery state shown in FIG. 14A. A loosening of the holding connection 7a, 20b by the radial release of the arms 20a is prevented by the holding sleeve 18 surrounding the click pin 20.

Figure 14B:
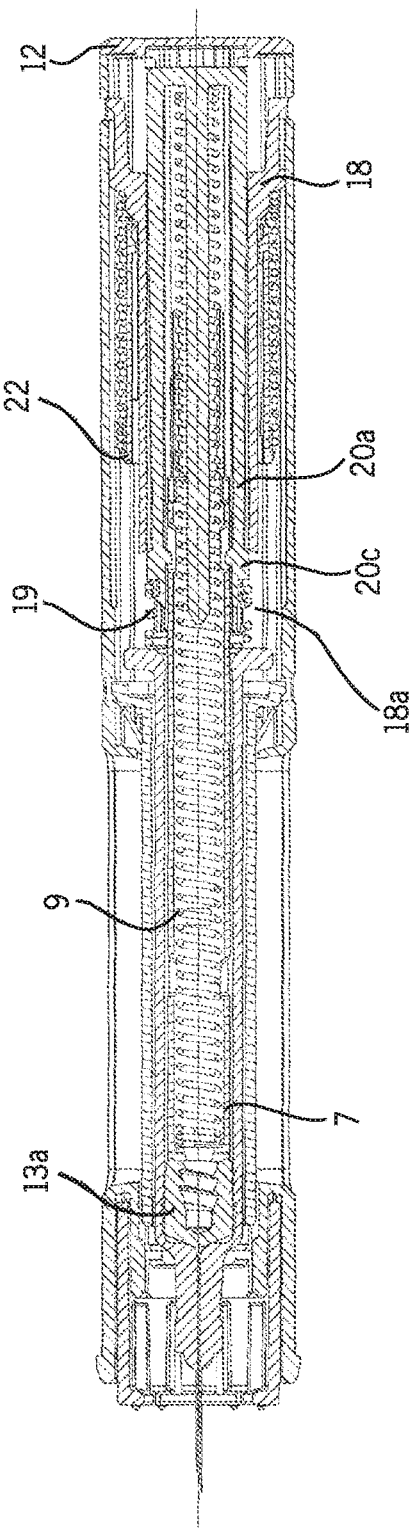
FIG. 14B shows the injection device, in accordance with FIG. 14A, in the dispensed state before the end click.

If the housing 2 of the injection device is pressed so far on an injection site that the needle protective sleeve 3 was almost completely, or completely, pushed into the housing 2, as shown in FIG. 14B, the automatic injection is triggered.

A release sleeve 22 is thereby axially pushed, in the proximal direction, against the force of the needle protective sleeve spring 10 within the housing 2 by the adjacent arms 3a of the needle protective sleeve 3 to such an extent that a holding element of the holding sleeve 18, which engages in the piston rod 7, is released.

Since the piston rod 7 is acted on by the injection spring 9 in the distal direction, relative to the housing 2, the then released piston rod 7 can be moved, in the distal direction, to the stopper 13a of the syringe 13 and can move this stopper 13a into the syringe 13, in order to carry out the dispensing. During the dispensing, the click pin 20 is entrained by the piston rod 7, until the arms 20a of the click pin can deflect radially in the free position 18a of the holding sleeve 18 and be held on the holding sleeve 18 by this intervention of the cams 20c that lie radially and externally on the arms 20a. A release of the arms 20a of the click pin 20, directed radially inwards, by the piston rod 7, lying on the inside on the cams 20b, is impossible until the piston rod 7 has been moved, in the distal direction, to such an extent that the complete dispensing has been carried out.

At the end of the dispensing, the arms 20a of the click pin 20 move radially inwards, since the piston rod 7 was moved, in the distal direction, to such an extent that either, in accordance with a non-depicted embodiment, the piston rod was already completely moved past the cam 20b, or, as shown in FIG. 14B, the inside cams 20b can be deflected back into openings or free positions on the piston rod 7. The click pin is thus no longer held by cams 20c or 20b and accelerates, in the proximal direction, due to the pretensioned syringe spring 19, in order to strike the holding sleeve 18 or, alternatively, the end cap 12 (not depicted) and thus produce an end click sound.

FIG. 15A shows another embodiment of a functional unit for the production of an end click. An injection spring is thereby placed under torsional stress between the piston rod 7 and a stabilization pin or the holding sleeve 18. The stabilization pin lies on the bottoms of the holding sleeve 18 and runs axially within the injection spring and is secured against twisting with the holding sleeve 18.

The piston rod 7 is conducted linearly in a linear guide 18b by means of a linear guide element 7f in the holding sleeve 18.

Figure 15B:
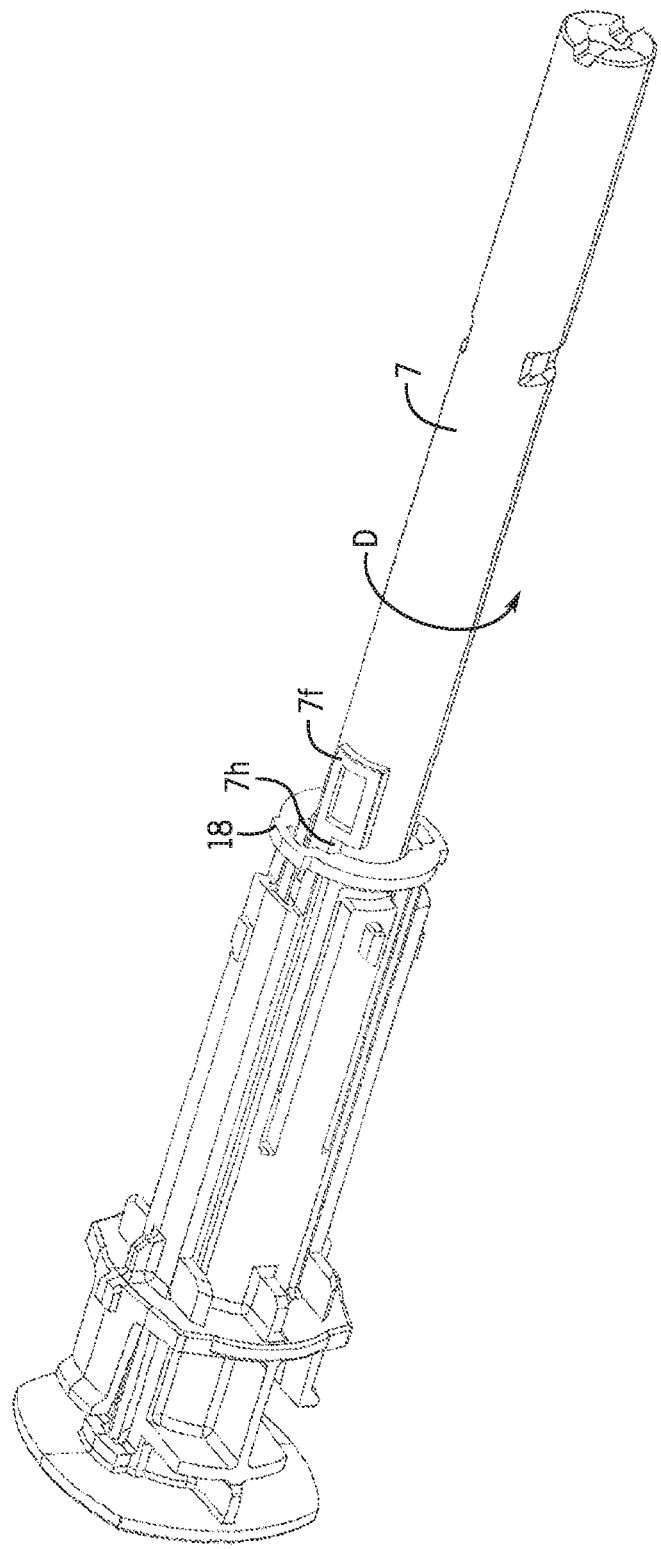
FIG. 15B shows the functional unit of FIG. 15A with a generated end click.

After the injection has been carried out by an axially forwards directed pushing out of the piston rod 7 from the holding sleeve, as shown in FIG. 15B, the piston rod 7 is decoupled by the movement of the linear guide element 7f out of the linear guide 18b. By the torsion moment of the injection spring 9, the piston rod 7 is rotated in the direction defined by the arrow indicating the rotational direction D and with a stop element 7h will strike, in the circumferential direction, against the holding sleeve 18 or a linear guide groove inner surface, wherein an end click can be produced.

Optionally, the piston rod 7 can thereby also rotate on the stopper 13a of the syringe 13.

Figure 16A:
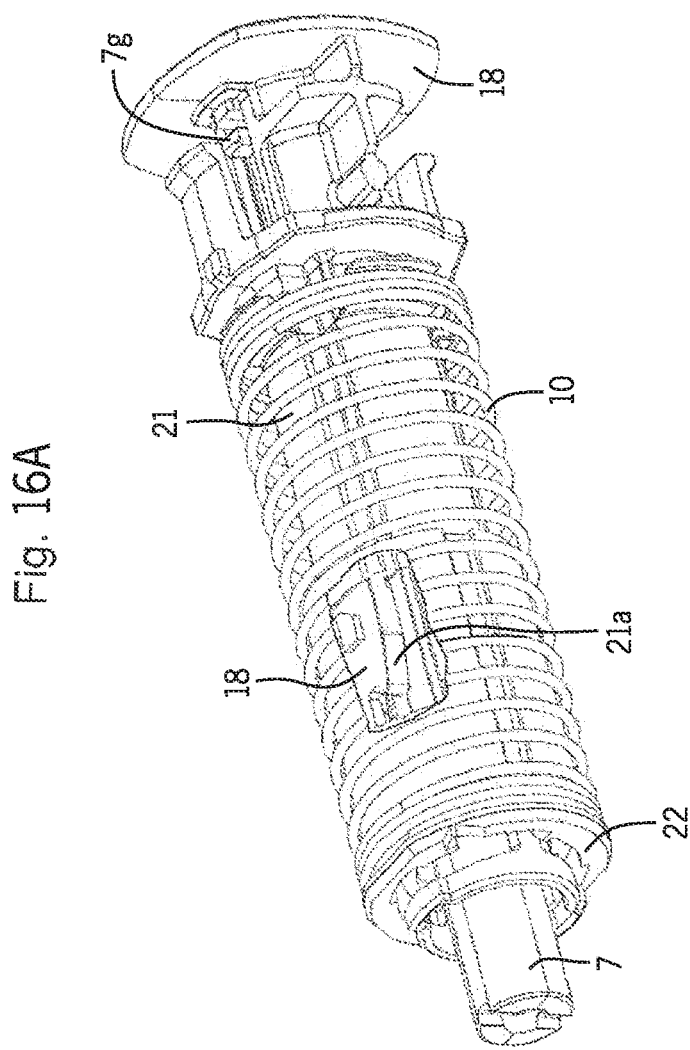
FIG. 16A shows an embodiment of a functional unit of an injection device in the delivery state for the generation of an end click by the energy of the needle protective sleeve spring.

FIG. 16A shows another embodiment of a functional unit for the production of an end click, wherein the energy for the end click is made available by the needle protective sleeve spring 10. The needle protective sleeve spring 10 is pretensioned between the release sleeve 22 in FIG. 16A and the click sleeve 21. The click sleeve 21 has hooks 21a, which engage in the holding sleeve 18.

Figure 16B:
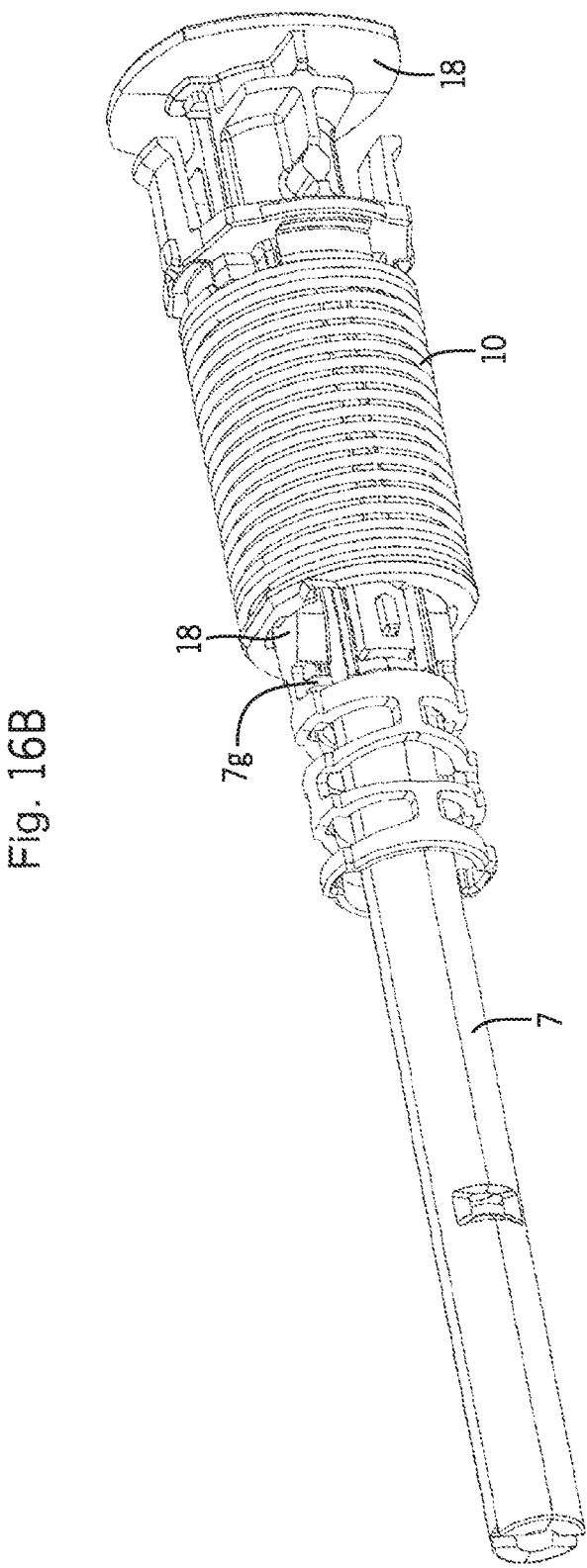
FIG. 16B shows the functional unit of FIG. 16A after the generated end click.

The piston rod 7 has a cam 7g, which presses the hooks 21a of the click sleeve 21, toward the end of the injection, as shown in FIG. 16B, by passing, proximally to distally (in FIG. 16B, from right to left), wherein they hang out from the holding sleeve 18 and thus the coupling of the click sleeve 21 with the holding sleeve 18 is loosened.

The click sleeve 21 is accelerated or moved, by the needle protective sleeve spring 10, toward the rear or, in a proximal direction, to a stop on the holding sleeve 18, wherein the end click is produced.

What is claimed is:

1. A device for releasing a substance by means of a release element, the device comprising:
    a displaceable protective element for the release element, the protective element being displaceable in a distal direction in order to cover the release element;
    a drive element in the form of a spring displacing the protective element in the distal direction in order to cover the release element; and
    a first feedback element driven by the drive element to produce an end signal when a predefined quantity of the substance has been released.

2. The device according to claim 1, wherein a second feedback element produces a start signal at a beginning of the release of the predefined quantity of the sub stance.

3. The device according to claim 2, further comprising a second drive element for releasing the substance.

4. The device according to claim 3, wherein the second feedback element is driven by the second drive element.

5. The device according to claim 4, further comprising a locking sleeve in a coupling with the second feedback element prior to the beginning of the release, wherein movement of the displaceable protective element in a proximal direction slaves the locking sleeve in movement and releases the coupling such that the second drive element moves the second feedback element in the proximal direction thereby causing the start signal to be produced.

6. The device according to claim 3, wherein the second drive element releases energy to the drive element before, during, or after the predefined quantity of the substance has been released.

7. The device according to claim 2, wherein one or more of the first feedback element or the second feedback element strikes a housing or a stationary element in the housing to produce one or more of the respective start signal or the end signal.

8. The device according to claim 2, further comprising a dampening element or a modulation element, by means of which one or more of the start signal or the end signal produced is modified.

9. The device according to claim 2, wherein one or more of the start signal or the end signal is one or more of an acoustical, an optical, or a tactile signal.

10. The device according to claim 1, wherein the protective element covers or surrounds the release element before the substance is released.

11. The device according to claim 1, further comprising a releasable holding device configured to hold the first feedback element until the predefined quantity of the substance has been released.

12. The device according to claim 11, wherein the releasable holding device and a piston rod cooperate to hold the first feedback element.

13. The device according to claim 12, wherein upon the piston rod moving in the distal direction to release the predefined quantity of the substance, the drive element moves the first feedback element in a proximal direction thereby causing the end signal to be produced.

14. The device according to claim 13, wherein after the predefined quantity of the substance has been released, the drive element moves the displaceable protective element in the distal direction to cover the release element.

15. The device according to claim 14, further comprising:
a second feedback element configured to produce a start signal at a beginning of the release of the predefined quantity of the substance; and
a second drive element for releasing the substance and for driving the second feedback element.

16. The device according to claim 15, further comprising a locking sleeve in a coupling with the second feedback element prior to the beginning of the release, wherein movement of the displaceable protective element in the proximal direction slaves the locking sleeve in movement and releases the coupling such that the second drive element moves the second feedback element in the proximal direction thereby causing the start signal to be produced.

17. The device according to claim 1, wherein the first feedback element is configured to move one or more of longitudinally along the device or rotationally in the device.

18. The device according to claim 1, wherein the protective element covers or surrounds the release element after the substance is released.

19. The device according to claim 1, wherein the first feedback element is accelerated by the drive element over a predefined distance.

* * * * *